United States Patent
Park et al.

(10) Patent No.: US 9,982,071 B2
(45) Date of Patent: *May 29, 2018

(54) CYCLIC OLEFIN COMPOUND HAVING PHOTOREACTIVE GROUP AND PHOTOREACTIVE POLYMER

(71) Applicant: LG CHEM, LTD., Seoul (KR)

(72) Inventors: Eun Seok Park, Daejeon (KR); Sung-Ho Chun, Daejeon (KR); Dai Seung Choi, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/911,462

(22) PCT Filed: Sep. 26, 2014

(86) PCT No.: PCT/KR2014/009047
§ 371 (c)(1),
(2) Date: Feb. 10, 2016

(87) PCT Pub. No.: WO2015/046966
PCT Pub. Date: Apr. 2, 2015

(65) Prior Publication Data
US 2016/0194418 A1 Jul. 7, 2016

(30) Foreign Application Priority Data

Sep. 30, 2013 (KR) .................. 10-2013-0116650
Sep. 25, 2014 (KR) .................. 10-2014-0128567

(51) Int. Cl.
| | | |
|---|---|---|
| *G02F 1/1333* | (2006.01) | |
| *C08F 120/40* | (2006.01) | |
| *C07C 57/26* | (2006.01) | |
| *C08G 61/08* | (2006.01) | |
| *C09K 19/56* | (2006.01) | |
| *C07C 69/618* | (2006.01) | |
| *C07D 319/06* | (2006.01) | |
| *G02B 5/32* | (2006.01) | |
| *G02F 1/13363* | (2006.01) | |
| *G02F 1/1337* | (2006.01) | |
| *G02B 5/30* | (2006.01) | |

(52) U.S. Cl.
CPC ............ *C08F 120/40* (2013.01); *C07C 57/26* (2013.01); *C07C 69/618* (2013.01); *C07D 319/06* (2013.01); *C08G 61/08* (2013.01); *C09K 19/56* (2013.01); *G02B 5/32* (2013.01); *C07C 2601/14* (2017.05); *C07C 2602/42* (2017.05); *C07C 2603/91* (2017.05); *C08G 2261/135* (2013.01); *C08G 2261/1426* (2013.01); *C08G 2261/418* (2013.01); *C08G 2261/74* (2013.01); *C08G 2261/76* (2013.01); *G02B 5/3083* (2013.01); *G02F 1/13363* (2013.01); *G02F 1/133788* (2013.01)

(58) Field of Classification Search
CPC ........ C08G 2261/135; C08G 2261/1426; C08G 2261/418; C08G 2261/74; C08G 2261/76; C08G 61/08; C08F 120/40; C07C 57/26; C07C 69/618; C07C 2601/14; C07C 2602/42; C07C 2603/91; G02F 1/1333; G02F 1/13363; G02F 1/133788; G02B 5/32; G02B 5/3083; C09K 19/56; C07D 319/06
USPC ....................... 252/299.01; 428/1.1
See application file for complete search history.

(56) References Cited

U.S. PATENT DOCUMENTS

| | | | |
|---|---|---|---|
| 6,169,152 B1 | 1/2001 | Sakai | |
| 8,946,366 B2 * | 2/2015 | Yoo ................. | C07C 69/734 525/326.7 |
| 9,150,678 B2 * | 10/2015 | Yoo ................. | C08F 132/08 |
| 9,151,988 B2 * | 10/2015 | Yoo ................. | C07C 69/734 |
| 2012/0010381 A1 | 1/2012 | Choi et al. | |
| 2012/0056183 A1 | 3/2012 | Mueller et al. | |
| 2012/0075560 A1 | 3/2012 | Yoo et al. | |
| 2012/0076953 A1 | 3/2012 | Cho et al. | |
| 2012/0149848 A1 | 6/2012 | Choi et al. | |
| 2016/0222147 A1 * | 8/2016 | Park ................. | C08F 220/40 |

FOREIGN PATENT DOCUMENTS

| | | |
|---|---|---|
| CN | 102417454 A | 4/2012 |
| JP | 03-220230 A | 9/1991 |
| JP | 2010-522253 A | 7/2010 |
| JP | 2012-072403 A | 4/2012 |
| JP | 2013-525566 A | 6/2013 |
| JP | 2013-525590 A | 6/2013 |
| KR | 10-2010-0021751 A | 2/2010 |
| KR | 10-1071401 B1 | 9/2011 |
| KR | 10-2012-0007564 A | 1/2012 |
| KR | 10-2012-0031882 A | 4/2012 |
| KR | 10-2012-0031912 A | 4/2012 |

(Continued)

OTHER PUBLICATIONS

"Synthesis and Nonlinear-Optical Properties of Vinyl-Addition Poly(norbornene)s"; Ki Hong Park, et al.; Macromolecules 2004, 37, 5163-5178.

*Primary Examiner* — Geraldina Visconti

(74) *Attorney, Agent, or Firm* — Dentons US LLP

(57) ABSTRACT

There are provided a novel cyclic olefin compound having a photoreactive group and a photoreactive polymer. The cyclic olefin compound is applicable to various photoreactions, such as of liquid crystal alignment layers and can be preferably used as a precursor of various organic compounds or polymers.

12 Claims, 1 Drawing Sheet

(56) References Cited

FOREIGN PATENT DOCUMENTS

| KR | 10-2012-0044883 A | 5/2012 |
|----|-------------------|--------|
| KR | 10-2013-0114121 A | 10/2013 |
| TW | 200407414 | 5/2004 |
| WO | 96-37526 A1 | 11/1996 |
| WO | 2012/044020 A2 | 4/2012 |
| WO | 2013/036901 A2 | 3/2013 |

* cited by examiner

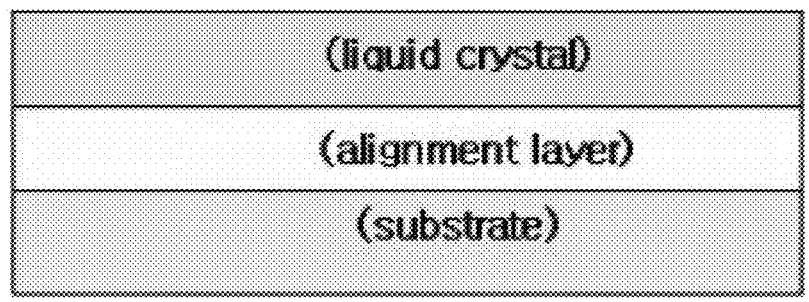

CYCLIC OLEFIN COMPOUND HAVING PHOTOREACTIVE GROUP AND PHOTOREACTIVE POLYMER

This application is a National Stage Entry of International Application No. PCT/KR 2014/009047, filed Sep. 26, 2014, and claims the benefit of Korean Application No. 10-2013-0116650, filed on Sep. 30, 2013, and Korean Application No. 10-2014-0128567, filed Sep. 25, 2014, all of which are hereby incorporated by reference in their entirety for all purposes as if fully set forth herein.

TECHNICAL FIELD

The present invention relates to a novel cyclic olefin compound having a photoreactive group and a photoreactive polymer.

More particularly, the present invention relates to a novel cyclic olefin compound having a photoreactive group and a photoreactive polymer prepared from the same that are applicable to various photoreactions, such as of liquid crystal alignment layers, or the like, and can also be preferably used as precursors of different organic compounds or polymers.

BACKGROUD

Recently, a variety of photoreactive compounds or polymers have been used in a wide range of optical applications, such as thin film transistor liquid crystal display (TFT-LCD), photoresist, and so forth.

TFT-LCDs, for example, have an alignment layer underlying a liquid crystal layer so as to use liquid crystals as optical switches. Recently, photoreactive polymers, or the like, are used in the alignment layer to employ UV-based photo-alignment.

As used herein, the term "photo-alignment" refers to a mechanism that functional groups (photoreactive groups) of a defined photoreactive polymer causes photoreactions by a linearly polarized UV light exposure, during which the polymer main chain is aligned in a defined direction, bringing about liquid crystal alignment.

For more effective photo-alignment to occur, the photoreactive polymer contained in the alignment layer is required to cause good interactions with the molecules in the liquid crystal layer and furthermore to possess a good photoreactivity.

With a gradual increase in the usage of photoreactive compounds or polymers in a wider variety of applications, there is a demand for various photoreactive compounds or polymers that have excellent photoreactivity to more different types of light (for example, omnidirectional polarized UV light, UV light of various wavelengths, etc.).

However, most of the existing photoreactive polymers do not have a good photoreactivity or cause enough interactions with liquid crystal molecules. Moreover, the development of photoreactive polymers with a good photoreactivity to various types of light has not been sufficiently conducted.

DISCLOSURE

Technical Problem

The present invention has been made in an effort to provide a novel cyclic olefin compound having a photoreactive group that is applicable to various photoreactions, such as of liquid crystal alignment layers, and can also be preferably used as precursors of different organic compounds or polymers.

Further, the present invention has been made in an effort to provide a photoreactive polymer capable of easily adjusting photoreactivity to various types of light and being used in an alignment layer, or the like, to exhibit an improved interaction with liquid crystal molecules and excellent photoreactivity.

In addition, the present invention has been made in an effort to provide an alignment layer comprising the photoreactive polymer.

Technical Solution

An exemplary embodiment of the present invention provides a cyclic olefin compound having a photoreactive group represented by the following Chemical Formula 1:

[Chemical Formula 1]

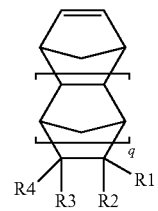

in Chemical Formula 1, q is an integer from 0 to 4;

at least one of R1, R2, R3, and R4 is a radical represented by the following Chemical Formula 1a, among R1 to R4, the remainders other than the radical of Chemical Formula 1a are the same as or different from one another and each independently selected from the group consisting of hydrogen; halogen; substituted or unsubstituted linear or branched alkyl having 1 to 20 carbon atoms; substituted or unsubstituted linear or branched alkenyl having 2 to 20 carbon atoms; substituted or unsubstituted linear or branched alkynyl having 2 to 20 carbon atoms; substituted or unsubstituted cycloalkyl having 3 to 12 carbon atoms; substituted or unsubstituted aryl having 6 to 40 carbon atoms; substituted or unsubstituted arylalkyl having 5 to 12 carbon atoms; and a polar functional group including at least one selected from oxygen, nitrogen, phosphorus, sulfur, silicon, and boron, when R1 to R4 are not hydrogen, halogen, or a polar functional group, at least one combination of R1 and R2 or R3 and R4 is bonded to each other to form an alkylidene group having 1 to 10 carbon atoms, or R1 or R2 is bonded to either R3 or R4 to form a saturated or unsaturated aliphatic ring having 4 to 12 carbon atoms or an aromatic ring having 6 to 24 carbon atoms,

[Chemical Formula 1a]

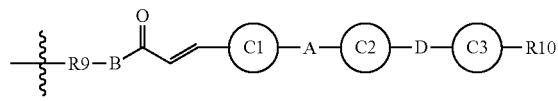

in Chemical Formula 1a,

A is selected from the group consisting of a single bond, substituted or unsubstituted alkylene having 1 to 20 carbon atoms, substituted or unsubstituted alkenylene having 2 to 20 carbon atoms, substituted or unsubstituted cycloalkylene having 3 to 12 carbon atoms, substituted or unsubstituted arylene having 6 to 40 carbon atoms, substituted or unsubstituted arylalkylene having 7 to 15 carbon atoms, and substituted or unsubstituted alkynylene having 2 to 20 carbon atoms, B is a single bond, oxygen, sulfur, —NH—, or 1,4-phenylene, R9 is selected from the group consisting of a single bond, substituted or unsubstituted alkylene having 1 to 20 carbon atoms, substituted or unsubstituted alkenylene having 2 to 20 carbon atoms, substituted or unsubstituted cycloalkylene having 3 to 12 carbon atoms, substituted or unsubstituted arylene having 6 to 40 carbon atoms, substituted or unsubstituted arylalkylene having 7 to 15 carbon atoms, and substituted or unsubstituted alkynylene having 2 to 20 carbon atoms, C1 is C6-C40 arylene unsubstituted or substituted with at least one functional group selected from the group consisting of halogen, cyano, and nitro; C7-C15 arylalkylene unsubstituted or substituted with at least one functional group selected from halogen, cyano, and nitro; or C4-C40 heteroarylene including a hetero element in Group 14, 15 or 16, C2 is C6-C40 arylene unsubstituted or substituted with at least one functional group selected from the group consisting of halogen, cyano, and nitro; C4-C40 heteroarylene including a hetero element in Group 14, 15 or 16; C5-C10 cycloalkylene; or C4-C40 heterocycloalkylene including a hetero element in Group 14, 15, or 16, C3 is C5-C10 cycloalkylene unsubstituted or substituted with at least one functional group selected from the group consisting of halogen, cyano, and nitro, or C4-C40 heterocycloalkylene including a hetero element in Group 14, 15, or 16, D is selected from the group consisting of a single bond, substituted or unsubstituted alkylene having 1 to 20 carbon atoms, substituted or unsubstituted alkenylene having 2 to 20 carbon atoms, substituted or unsubstituted cycloalkylene having 3 to 12 carbon atoms, substituted or unsubstituted arylene having 6 to 40 carbon atoms, substituted or unsubstituted arylalkylene having 7 to 15 carbon atoms, and substituted or unsubstituted alkynylene having 2 to 20 carbon atoms, and, R10 is selected from the group consisting of hydrogen; halogen; cyano; nitro; —NCS; substituted or unsubstituted linear or branched alkyl having 1 to 20 carbon atoms; substituted or unsubstituted alkoxy having 1 to 20 carbon atoms; and substituted or unsubstituted aryloxy having 6 to 30 carbon atoms.

Another exemplary embodiment of the present invention provides a photoreactive polymer comprising a repeating unit represented by following Chemical Formula 2a or 2b:

[Chemical Formula 2a]

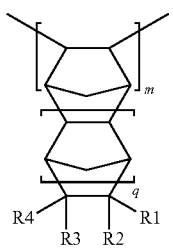

[Chemical Formula 2b]

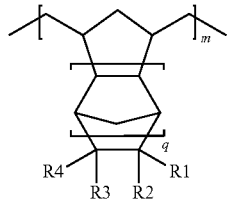

in Chemical Formulas 2a and 2b, each independently, m is 50 to 5000, and q, R1, R2, R3, and R4 are as defined in Chemical Formula 1.

Another exemplary embodiment of the present invention provides an alignment layer comprising the photoreactive polymer.

Another exemplary embodiment of the present invention provides a liquid crystal retardation film comprising the alignment layer and a liquid crystal layer on the alignment layer.

Another exemplary embodiment of the present invention provides a display device comprising the alignment layer.

Advantageous Effects

The cyclic olefin compound according to the present invention may have a photoreactive group such as a cinnamate or chalcone structure depending on the structure of Chemical Formula 1a. Therefore, the cyclic olefin compound exhibits excellent photoreactivity by itself, such that the cyclic olefin compound is applicable to various photoreactions, such as of liquid crystal alignment layers and can be preferably used as a precursor of various organic compounds or polymers.

In addition, the cyclic olefin compound may have the photoreactive group, such as a cinnamate or chalcone structure, additionally substituted with cyclic substituents (C2 and C3). In general, liquid crystal molecules have an aromatic or aliphatic ring, and the cyclic olefin compound or the photoreactive polymer obtained from the cyclic olefin compound may have improved interactions with the liquid crystal molecules due to the cyclic substituents (C2 and C3) additionally substituted in the cyclic olefin compound, such that photo-alignment may be more effectively performed.

In addition, various photoreactive compounds or polymers, or the like, having excellent photoreactivity to different types of lights may be provided by adjusting a structure of Chemical Formula 1a of the cyclic olefin compound.

BRIEF DESCRIPTION OF THE DRAWINGS

FIG. 1 is a schematic diagram showing a structure of an alignment layer according to an exemplary embodiment of the present invention.

BEST MODE

Terms used in the present specification are used in order to describe specific exemplary embodiments rather than limiting the present invention. Singular forms used in the specification are intended to include plural forms unless the context clearly indicates otherwise. Terms such as "comprise", "include", "have", and the like, used in the present specification will imply the existence of stated features, numbers, steps, configuration elements, or a combination thereof, but do not exclude presence or addition of one or more other features, numbers, steps, configuration elements, or a combination thereof.

Further, in the present specification, each layer or element is referred to as being formed "on" or "over" respective layers or elements, which means that each layer or element may be formed directly on respective layers or elements or another layer or element may be additionally formed between respective layers or on a target material or substrate.

The present invention may be variously modified and have various types, and specific exemplary embodiments of the present invention will be descried in detail. However, the present invention is not limited to the exemplary embodiments described herein, but all of the modifications, equivalents, and substitutions within the spirit and scope of the present invention are also included in the present invention.

Prior to a detailed description of the present invention, each substituent used in the present specification will be specifically defined as follows:

First, the term "alkyl" as used herein refers to a monovalent linear or branched saturated hydrocarbon portion having 1 to 20 carbon atoms, preferably, 1 to 10 carbon atoms, more preferably 1 to 6 carbon atoms. The alkyl group inclusively refers to an alkyl group unsubstituted or additionally substituted with specific substituents to be described later. The examples of the alkyl group may include methyl, ethyl, propyl, 2-propyl, n-butyl, iso-butyl, tert-butyl, pentyl, hexyl, dodecyl, fluoromethyl, difluoromethyl, trifluoromethyl, chloromethyl, dichloromethyl, trichloromethyl, iodomethyl, bromomethyl, or the like.

First, the term "alkenyl" as used herein refers to a monovalent linear or branched hydrocarbon portion having 2 to 20 carbon atoms, preferably, 2 to 10 carbon atoms, more preferably 2 to 6 carbon atoms with at least one carbon-carbon double bond. The alkenyl group may form a bonding through carbon atoms including a carbon-carbon double bond or through saturated carbon atoms. The alkenyl group inclusively refers to an alkenyl group unsubstituted or additionally substituted with a specific substituent to be described later. The examples of the alkenyl group may include ethenyl, 1-propenyl, 2-propenyl, 2-butenyl, 3-butenyl, pentenyl, 5-hexenyl, dodecenyl, or the like.

The term "cycloalkyl" as used herein refers to a monovalent saturated or unsaturated mono-, bi- or tri-cyclic non-aromatic hydrocarbon portion having 3 to 12 ring-carbon atoms, and may inclusively refer to a cycloalkyl group additionally substituted with a specific substituent to be described later. The examples of the cycloalkyl group may include cyclopropyl, cyclobutyl, cyclopentyl, cyclopentenyl, cyclohexyl, cyclohexenyl, cycloheptyl, cyclooctyl, decahydronaphthalenyl, adamantyl, norbornyl (that is, bicyclo[2,2,1]hept-5-enyl), or the like.

The term "aryl" as used herein refers to a monovalent mono-, bi- or tri-cyclic aromatic hydrocarbon portion having 6 to 40 ring atoms, preferably 6 to 12 ring atoms, and may inclusively refer to an aryl group additionally substituted with a specific substituent to be described later. The examples of the aryl group may include phenyl, naphthalenyl, fluorenyl, or the like.

The term "alkoxyaryl" as used herein refers to the above-defined aryl group in which at least one hydrogen atom is substituted by an alkoxy group. The examples of the alkoxyaryl group may include methoxyphenyl, ethoxyphenyl, propoxyphenyl, butoxyphenyl, pentoxyphenyl, hextoxyphenyl, heptoxy, octoxy, nanoxy, methoxybiphenyl, methoxynaphthalenyl, methoxyfluorenyl, methoxyanthracenyl, or the like.

The term "arylalkyl" as used herein refers to the above-defined alkyl group in which at least one hydrogen atom is substituted by an aryl group, and may inclusively refer to an arylalkyl group additionally substituted with a specific substituent to be described later. The examples of the arylalkyl may include benzyl, benzhydryl, trityl, or the like.

The term "alkynyl" as used herein refers to a monovalent linear or branched hydrocarbon portion having 2 to 20 carbon atoms, preferably 2 to 10 carbon atoms, more preferably 2 to 6 carbon atoms with at least one carbon-carbon triple bond. The alkynyl group may form a bonding through carbon atoms including a carbon-carbon triple bond or through saturated carbon atoms. The alkynyl group may inclusively refer to an alkynyl group additionally substituted with a specific substituent to be described later. The examples of the alkynyl group may include ethynyl, propynyl, or the like.

The term "alkylene" as used herein refers to a divalent linear or branched saturated hydrocarbon portion having 1 to 20 carbon atoms, preferably 1 to 10 carbon atoms, more preferably 1 to 6 carbon atoms. The alkylene group may inclusively refer to an alkylene group additionally substituted with a specific substituent to be described later. The examples of the alkylene group may include methylene, ethylene, propylene, butylene, hexylene, or the like.

The term "alkenylene" as used herein refers to a divalent linear or branched hydrocarbon portion having 2 to 20 carbon atoms, preferably 2 to 10 carbon atoms, more preferably 2 to 6 carbon atoms with at least one carbon-carbon double bond. The alkenylene group may form a bonding through carbon atoms including a carbon-carbon double bond and/or through saturated carbon atoms. The alkenylene group inclusively refers to an alkenylene group additionally substituted with a specific substituent to be described later.

The term "cycloalkylene" as used herein refers to a divalent saturated or unsaturated mono-, bi- or tri-cyclic non-aromatic hydrocarbon portion having 3 to 12 ring-carbon atoms, and may inclusively refer to a cycloalkylene group additionally substituted with a specific substituent to be described below. The examples of the cycloalkylene group may include cyclopropylene, cyclobutylene, or the like.

The term "arylene" as used herein refers to a divalent mono-, bi- or tri-cyclic aromatic hydrocarbon portion having 6 to 20 ring atoms, preferably 6 to 12 ring atoms and may inclusively refer to an arylene group additionally substituted with a specific substituent, as will be described later. The aromatic portion includes carbon atoms only. The examples of the arylene group may include phenylene, or the like.

The term "arylalkylene" as used herein refers to a divalent portion of the above-defined alkyl group in which at least one hydrogen atom is substituted by an aryl group, and may inclusively refer to an arylalkylene group additionally substituted with a specific substituent to be described later. The examples of the arylalkylene group may include benzylene, or the like.

The term "alkynylene" as used herein refers to a divalent linear or branched hydrocarbon portion having 2 to 20 carbon atoms, preferably 2 to 10 carbon atoms, more preferably 2 to 6 carbon atoms with at least one carbon-carbon triple bond. The alkynylene group may form a bonding through carbon atoms including a carbon-carbon triple bond or through saturated carbon atoms. The alkynylene group may inclusively refer to an alkynylene group additionally substituted with a specific substituent to be described later. The examples of the alkynylene group may include ethynylene, propynylene, or the like.

In the above description, the phrase "a substituent is substituted or unsubstituted" has an inclusive meaning that the substituent is or isn't additionally substituted with the substituent itself or another defined substituent. Unless otherwise defined in the present specification, the examples of the substituent used as an additional substituent for each substituent may include halogen, alkyl, alkenyl, alkynyl, haloalkyl, haloalkenyl, haloalkynyl, aryl, haloaryl, arylalkyl, haloarylalkyl, alkoxy, haloalkoxy, carbonyloxy, halocarbonyloxy, aryloxy, haloaryloxy, silyl, siloxy, or "a polar functional group including oxygen, nitrogen, phosphorus, sulfur, silicon, or boron" to be described later.

Hereinafter, a cyclic olefin compound having a photoreactive group, a photoreactive polymer, and an alignment layer according to the exemplary embodiments of the present invention will be described in detail.

In accordance with an exemplary embodiment of the present invention, there is provided a cyclic olefin compound having a photoreactive group represented by the following Chemical Formula 1:

[Chemical Formula 1]

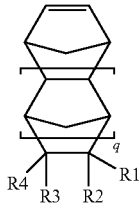

in Chemical Formula 1,
q is an integer from 0 to 4;
at least one of R1, R2, R3, and R4 is a radical represented by the following Chemical Formula 1a,
among R1 to R4, the remainders other than the radical of Chemical Formula 1a are the same as or different from one another and independently selected from the group consisting of hydrogen; halogen; substituted or unsubstituted linear or branched alkyl having 1 to 20 carbon atoms; substituted or unsubstituted linear or branched alkenyl having 2 to 20 carbon atoms; substituted or unsubstituted linear or branched alkynyl having 2 to 20 carbon atoms; substituted or unsubstituted cycloalkyl having 3 to 12 carbon atoms; substituted or unsubstituted aryl having 6 to 40 carbon atoms; substituted or unsubstituted arylalkyl having 5 to 12 carbon atoms; and a polar functional group including at least one selected from oxygen, nitrogen, phosphorus, sulfur, silicon, and boron,
when R1 to R4 are not hydrogen, halogen, or a polar functional group, at least one combination of R1 and R2 or R3 and R4 is bonded to each other to form an alkylidene group having 1 to 10 carbon atoms, or R1 or R2 is bonded to either R3 or R4 to form a saturated or unsaturated aliphatic ring having 4 to 12 carbon atoms or an aromatic ring having 6 to 24 carbon atoms,

[Chemical Formula 1a]

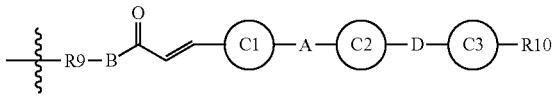

in Chemical Formula 1a,
A is selected from the group consisting of a single bond, substituted or unsubstituted alkylene having 1 to 20 carbon atoms, substituted or unsubstituted alkenylene having 2 to 20 carbon atoms, substituted or unsubstituted cycloalkylene having 3 to 12 carbon atoms, substituted or unsubstituted arylene having 6 to 40 carbon atoms, substituted or unsubstituted arylalkylene having 7 to 15 carbon atoms, and substituted or unsubstituted alkynylene having 2 to 20 carbon atoms, B is a single bond, oxygen, sulfur, —NH—, or 1,4-phenylene, R9 is selected from the group consisting of a single bond, substituted or unsubstituted alkylene having 1 to 20 carbon atoms, substituted or unsubstituted alkenylene having 2 to 20 carbon atoms, substituted or unsubstituted cycloalkylene having 3 to 12 carbon atoms, substituted or unsubstituted arylene having 6 to 40 carbon atoms, substituted or unsubstituted arylalkylene having 7 to 15 carbon atoms, and substituted or unsubstituted alkynylene having 2 to 20 carbon atoms, C1 is C6-C40 arylene unsubstituted or substituted with at least one functional group selected from the group consisting of halogen, cyano, and nitro; C7-C15 arylalkylene unsubstituted or substituted with at least one functional group selected from halogen, cyano, and nitro; or C4-C40 heteroarylene including a hetero element in Group 14, 15 or 16, C2 is C6-C40 arylene unsubstituted or substituted with at least one functional group selected from the group consisting of halogen, cyano, and nitro; C4-C40 heteroarylene including a hetero element in Group 14, 15 or 16; C5-C10 cycloalkylene; or C4-C40 heterocycloalkylene including a hetero element in Group 14, 15, or 16, C3 is C5-C10 cycloalkylene unsubstituted or substituted with at least one functional group selected from the group consisting of halogen, cyano, and nitro, or C4-C40 heterocycloalkylene including a hetero element in Group 14, 15, or 16, D is selected from the group consisting of a single bond, substituted or unsubstituted alkylene having 1 to 20 carbon atoms, substituted or unsubstituted alkenylene having 2 to 20 carbon atoms, substituted or unsubstituted cycloalkylene having 3 to 12 carbon atoms, substituted or unsubstituted arylene having 6 to 40 carbon atoms, substituted or unsubstituted arylalkylene having 7 to 15 carbon atoms, and substituted or unsubstituted alkynylene having 2 to 20 carbon atoms, and R10 is selected from the group consisting of hydrogen; halogen; cyano; nitro; —NCS; substituted or unsubstituted linear or branched alkyl having 1 to 20 carbon atoms; substituted or unsubstituted alkoxy having 1 to 20 carbon atoms; and substituted or unsubstituted aryloxy having 6 to 30 carbon atoms.

The compound as described above may have a chemical structure in which a predetermined photoreactive group (Chemical Formula 1a), for example, a cinnamate or chalcone structure is introduced in a cyclic olefin structure capable of being used as a precursor of various compounds or a monomer of polymers, or the like. The cyclic olefin compound of Chemical Formula 1 may be used as a photoreactive compound by itself due to the chemical structure in which the photoreactive group is introduced as described above.

In addition, due to structural characteristics of the cyclic olefin applicable as a precursor, or the like, various compounds or polymers may be prepared from the cyclic olefin compound, and the prepared compound or polymer may also have excellent photoreactivity due to the photoreactive group. Therefore, various photoreactive compounds or polymers, or the like, capable of being applied to various optical application fields may be prepared using the cyclic olefin compound.

In addition, the cyclic olefin compound may have a chemical structure in which a cyclic substituent (C2) is further bonded to the photoreactive group such as the cinnamate or chalcone structure via a specific functional group A. In addition, the cyclic olefin compound may have a chemical structure in which a cyclic substituent (C3) is further bonded to the photoreactive group via a specific functional group D. In general, liquid crystal molecules have an aromatic or aliphatic ring, and the cyclic olefin compound or the photoreactive polymer obtained from the cyclic olefin compound may have improved interactions with the liquid crystal molecules due to the aromatic or aliphatic cyclic substituent (C2 or C3) capable of being additionally bonded to the cyclic olefin compound, such that photo-alignment may be more effectively performed. Therefore, the cyclic olefin compound and the photoreactive polymer obtained from the cyclic olefin compound may be preferably used in the liquid crystal alignment layer, or the like, to thereby have improved interactions with the liquid crystal molecules and excellent photoreactivity.

In addition, photoreactivity of the cyclic olefin compound itself and the photoreactive polymer obtained therefrom may be easily adjusted by adjusting a structure of Chemical Formula 1a of the cyclic olefin compound, particularly, the kind of the additionally substituted cyclic substituents (C2 and C3), or the like, using various arylenes, heteroarylenes, cycloalkylenes, or heterocycloalkylenes. Therefore, various photoreactive compounds or polymers, or the like, having excellent photoreactivity to various types of light, may be obtained from the cyclic olefin compound as described above.

Hereinafter, the cyclic olefin compound, the photoreactive polymer obtained from the cyclic olefin compound, and the like, will be described in more detail.

In the cyclic olefin compound, a polar functional group used as a substituent for the R1 to R4, that is, a polar functional group including at least one selected from oxygen, nitrogen, phosphorus, sulfur, silicon, and boron may be selected from the group consisting of the following functional groups, or may be selected from various other polar functional groups including at least one of oxygen, nitrogen, phosphorus, sulfur, silicon, or boron except for the following functional groups:

—$OR_6$, —$OC(O)OR_6$, —$R_5OC(O)OR_6$, —$C(O)OR_6$, —$R_5C(O)OR_6$, —$C(O)R_6$, —$R_5C(O)R_6$, —$OC(O)R_6$, —$R_5OC(O)R_6$, —$(R_5O)_p$—$OR_6$, —$(OR_5)_p$—$OR_6$, —$C(O)$—$O$—$C(O)R_6$, —$R_5C(O)$—$O$—$C(O)R_6$, —$SR_6$, —$R_5SR_6$, —$SSR_6$, —$R_5SSR_6$, —$S(=O)R_6$, —$R_5S(=O)R_6$, —$R_5C(=S)R_6$—, —$R_5C(=S)SR_6$, —$R_5SO_3R_6$, —$SO_3R_6$, —$R_5N=C=S$, —$N=C=S$, —NCO, —$R_5$—NCO, —CN, —$R_5$CN, —NNC(=S)$R_6$, —$R_5$NNC(=S)$R_6$, —$NO_2$, —$R_5NO_2$,

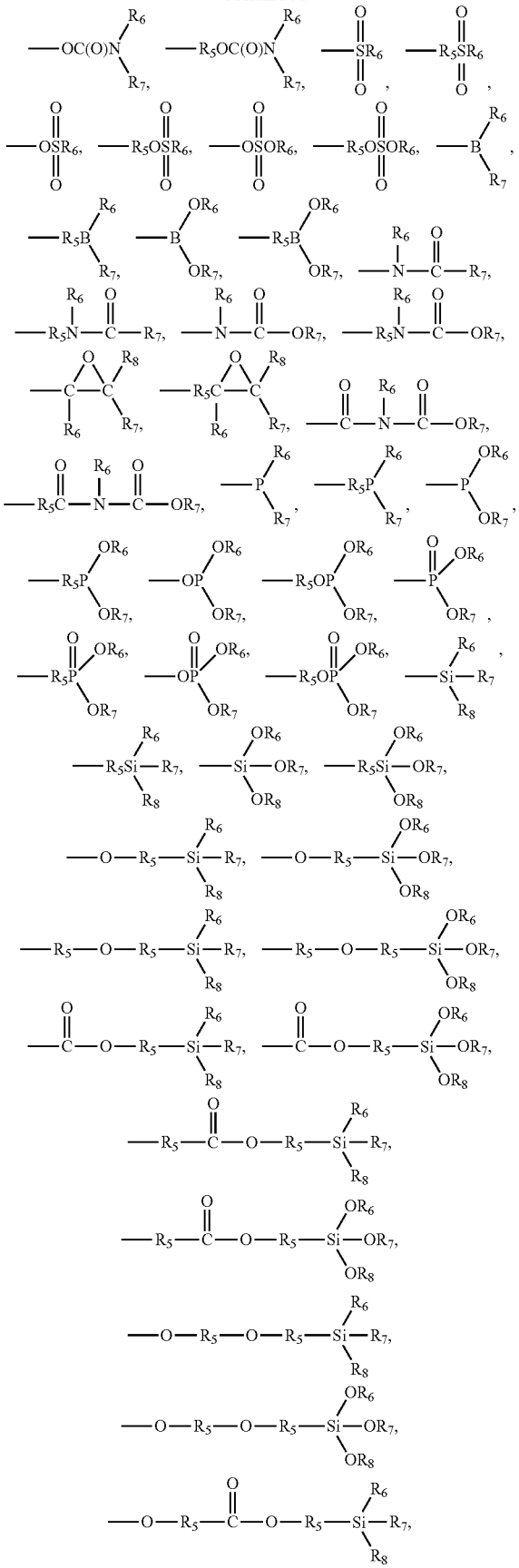

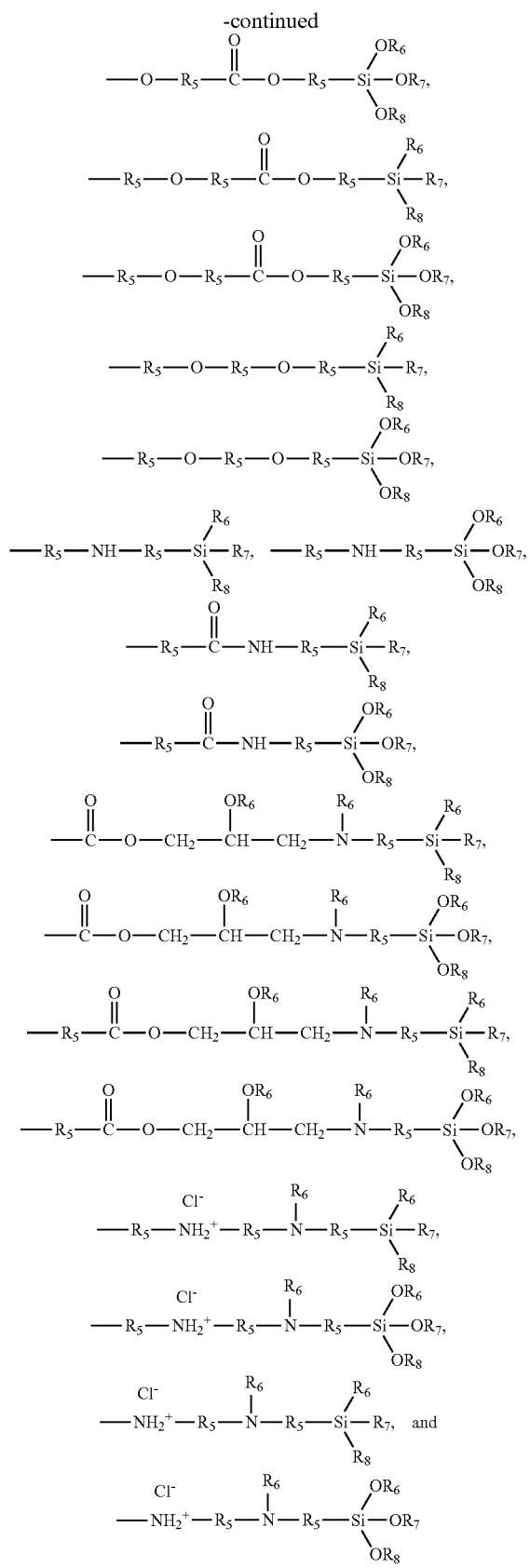

in the polar functional groups, each p is independently an integer from 1 to 10, $R_5$ is substituted or unsubstituted linear or branched alkylene having 1 to 20 carbon atoms; substituted or unsubstituted linear or branched alkenylene having 2 to 20 carbon atoms; substituted or unsubstituted linear or branched alkynylene having 2 to 20 carbon atoms; substituted or unsubstituted cycloalkylene having 3 to 12 carbon atoms; substituted or unsubstituted arylene having 6 to 40 carbon atoms; substituted or unsubstituted carbonyloxylene having 1 to 20 carbon atoms; or substituted or unsubstituted alkoxylene having 1 to 20 carbon atoms; and $R_6$, $R_7$, and $R_8$ are each independently selected from the group consisting of hydrogen; halogen; substituted or unsubstituted linear or branched alkyl having 1 to 20 carbon atoms; substituted or unsubstituted linear or branched alkenyl having 2 to 20 carbon atoms; substituted or unsubstituted linear or branched alkynyl having 2 to 20 carbon atoms; substituted or unsubstituted cycloalkyl having 3 to 12 carbon atoms; substituted or unsubstituted aryl having 6 to 40 carbon atoms; substituted or unsubstituted alkoxy having 1 to 20 carbon atoms; and substituted or unsubstituted carbonyloxy having 1 to 20 carbon atoms.

Further, in the cyclic olefin compound, C1 may be C6-C40 arylene unsubstituted or substituted with at least one functional group selected from the group consisting of halogen, cyano, and nitro (for example, substituted or unsubstituted phenylene, 1,4- or 2,6-naphthylene, or the like); C7-C15 arylalkylene unsubstituted or substituted with at least one functional group selected from the group consisting of halogen, cyano, and nitro; or C4-C40 heteroarylene including a hetero element in Group 14, 15 or 16 (for example, 2,5-thiophenediyl, 2,5-furanylene, or the like).

In addition, C2 bonded to C1 via the specific functional group A may be C6-C40 arylene unsubstituted or substituted with at least one functional group selected from the group consisting of halogen, cyano, and nitro (for example, substituted or unsubstituted phenylene, 1,4- or 2,6-naphthylene, or the like); C4-C40 heteroarylene including a hetero element in Group 14, 15 or 16 (for example, 2,5-thiophenediyl, 2,5-furanylene, or the like); C5-C10 cycloalkylene (for example, cyclohexyl, or the like); or C4-C40 heterocycloalkylene including a hetero element in Group 14, 15 or 16 (for example, 1,3-dioxyl).

Further, C3 bonded to C2 via the specific functional group D may be C5-C10 cycloalkylene unsubstituted or substituted with at least one functional group selected from the group consisting of halogen, cyano, and nitro (for example, cyclohexyl, or the like); or C4-C40 heterocycloalkylene including a hetero element in Group 14, 15 or 16 (for example, 1,3-dioxyl).

In addition, R10 may be selected from the group consisting of hydrogen; halogen; cyano; nitro; —NCS; substituted or unsubstituted linear or branched alkyl having 1 to 20 carbon atoms; substituted or unsubstituted alkoxy having 1 to 20 carbon atoms; and substituted or unsubstituted aryloxy having 6 to 30 carbon atoms.

The above-mentioned cyclic olefin compound may be prepared by a general method of introducing a predetermined substituent, more specifically, the photoreactive group of Chemical Formula 1a, or the like, in cyclic olefin, for example, a norbornene based compound. For example, the cyclic olefin compound may be prepared by performing a condensation reaction of a norbornene alkylol such as norbornene methanol, or the like, and a carboxylic acid compound or an acyl chloride compound having a photoreactive group corresponding to Chemical Formula 1a. Otherwise, the above-mentioned cyclic olefin compound may be prepared by introducing the photoreactive group of Chemical Formula 1 depending on the structure and type of the photoreactive group of Chemical Formula 1a using various methods.

In accordance with another exemplary embodiment of the present invention, there is provided a photoreactive polymer comprising a repeating unit represented by following Chemical Formula 2a or 2b:

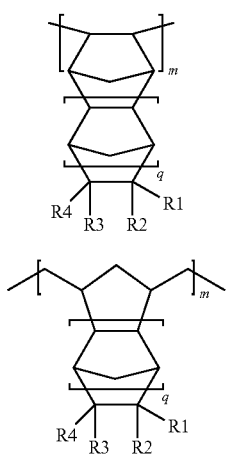

[Chemical Formula 2a]

[Chemical Formula 2b]

in Chemical Formulas 2a and 2b, each independently, m is 50 to 5,000, and q, R1, R2, R3, and R4 are as defined in Chemical Formula 1.

The above-mentioned photoreactive polymer, which includes a repeating unit derived from the cyclic olefin compound as described above, may exhibit excellent photoreactivity and have the structure of Chemical Formula 1a, particularly, the cyclic substituent (C2) additionally bonded thereto via the specific functional group A and the cyclic substituent (C3) bonded thereto via the specific functional group D, such that the photoreactive polymer may have improved interactions with the liquid crystal molecules and excellent photoreactivity. In addition, excellent photoreactivity to various types of light may be exhibited by selecting and adjusting the cyclic substitutents C2 and C3 rings from various arylenes, heteroarylenes, cycloalkylenes, and heterocycloalkylenes.

Further, the photoreactive polymer includes a norbonene-based repeating unit of Chemical Formula 2a or 2b as a main repeating unit. Since this norbonene-based repeating unit is structurally rigid, and the photoreactive polymer including the norbonene-based repeating unit has a relative high glass transition temperature (Tg) of about 300° C. or more, preferably about 300 to 350° C., the photoreactive polymer may have more excellent thermal stability as compared to the existing known photoreactive polymer, or the like. In addition, due to structural characteristics that a photoreactive group is bonded to the norbornene-based repeating unit, the photoreactive polymer has the photoreactive group relatively free to move in the main chain of the polymer, thereby exhibiting an excellent alignment property.

Therefore, the photoreactive polymer may be preferably used in a liquid crystal alignment layer for photo-alignment, and preferably applied to other various optical application fields.

Since a definition of each substituent bonded to the photoreactive polymer is specified above in detail in regard to Chemical Formula 1, a description thereof will be omitted.

In addition, the photoreactive polymer may include only at least one repeating unit selected from the group consisting of the repeating units of Chemical Formula 2a or 2b, but may also be a polymer further including another type of repeating units. The examples of this repeating unit may include any olefin-, acrylate- or cyclic-olefin-based repeating unit with or without a bonding to cinnamate-, chalcone- or azo-based photoreactive groups. The exemplary repeating units are disclosed in Korean Patent Laid-Open Publication No. 2010-0021751, or the like.

However, in order to prevent a deterioration in excellent photoreactivity, and the like, pertaining to the repeating unit of Chemical Formula 2a or 2b, the photoreactive polymer may include at least about 50 mol %, more specifically about 50 to about 100 mol %, preferably at least about 70 mol % of the repeating unit of the formula 2a or 2b.

In addition, the repeating unit of Chemical formula 2a or 2b constituting the photoreactive polymer has a degree of polymerization in the range of about 50 to about 5,000, preferably about 100 to about 4,000, and more preferably about 1,000 to about 3,000. In addition, the photoreactive polymer may have a weight average molecular weight of about 10,000 to 1,000,000, preferably about 20,000 to 500,000. Therefore, the photoreactive polymer may be suitably contained in a coating composition for forming an alignment layer to exhibit an excellent coating property, and the alignment layer prepared therefrom may exhibit an excellent liquid crystal alignment property, or the like.

The above-mentioned photoreactive polymer may have photoreactivity upon exposure to a polarized light having a wavelength of about 150 to about 450 nm. For example, the photoreactive polymer may have photoreactivity upon exposure to a polarized light having a wavelength of about 200 to about 400 nm, more specifically about 250 to about 350 nm. In particular, the photoreactive polymer may have excellent photoreactivity to light having a wide wavelength range and omnidirectional polarized lights as described above by selecting and adjusting the cyclic substituent (C2) additionally bonded via the specific functional group A and the cyclic susbstituent (C3) additionally bonded via the specific functional group D among various arylenes, heteroarylenes, cycloalkylenes, and heterocycloalkylenes.

Meanwhile, in accordance with another exemplary embodiment of the present invention, there is provided a preparation method of the above-mentioned photoreactive polymer. As an example, the preparation method of a photoreactive polymer includes: performing an addition polymerization reaction of a monomer represented by Chemical Formula 1 in the presence of a catalyst composition containing a precatalyst including a transition metal in Group 10 and a cocatalyst to form a repeating unit of Chemical Formula 2a:

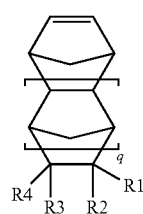

[Chemical Formula 1]

in Chemical Formula 1, q, R1, R2, R3, and R4 are as defined in Chemical Formula 2a.

In this case, the polymerization reaction may be carried out at a temperature of about 10 to about 200° C. The polymerization reaction temperature below 10° C. lowers the polymerization activity, while the temperature above 200° C. undesirably causes a cleavage of the catalyst.

In addition, the cocatalyst may include at least one selected from the group consisting of a first cocatalyst providing a Lewis base capable of forming a weak coordinate bond with a metal of the precatalyst; and a second cocatalyst providing a compound including a Group 15 electron donor ligand. Preferably, the cocatalyst may be a catalyst mixture including the first cocatalyst providing the Lewis base, and optionally the second cocatalyst providing a compound including a neutral Group 15 electron donor ligand.

In this case, the catalyst mixture may include, based on one mole of the precatalyst, about 1 to about 1,000 moles of the first cocatalyst and about 1 to about 1,000 moles of the second cocatalyst. The excessively low content of the first or second cocatalyst causes a failure to provide the catalyst activity enough, while an excess of the first or second cocatalyst rather deteriorates the catalyst activity.

In addition, the precatalyst including a transition metal in Group 10 may be a compound having a Lewis base functional group that is readily leaving from the central transition metal by the first cocatalyst providing a Lewis base and participating in a Lewis acid-base reaction to help the central transition metal to be changed into a catalyst active species. The examples of the precatalyst include allylpalladium chloride dimer ([(Allyl)Pd(Cl)]$_2$), palladium(II) acetate ((CH$_3$CO$_2$)$_2$Pd), palladium(II) acetylacetonate ([CH$_3$COCH═C(O—)CH$_3$]$_2$Pd), NiBr(NP(CH$_3$)$_3$)$_4$, [PdCl(NB)O(CH$_3$)]$_2$, or the like.

Further, the first cocatalyst providing a Lewis base capable of forming a weak coordinate bond with the metal of the precatalyst may be a compound that readily reacts with a Lewis base to provide vacancies in the transition metal and forms a weak coordinate bond with a transition metal compound in order to stabilize the resultant transition metal; or a compound providing such a compound. The examples of the first cocatalyst may include borane (e.g., B(C$_6$F$_5$)$_3$), borate (e.g., dimethylanilinium tetrakis(pentafluorophenyl)borate), alkylaluminum (e.g., methylaluminoxane (MAO) or Al(C$_2$H$_5$)$_3$), transition metal halide (e.g., AgSbF$_6$), or the like.

The examples of the second cocatalyst that provides a compound including a neutral Group 15 electron donor ligand may include alkyl phosphine, cycloalkyl phosphine, phenyl phosphine, or the like.

In addition, the first and second cocatalysts may be used separately, or used together to form a single salt compound to thereby be used as a compound for activating the catalyst. For example, there may be a compound prepared as an ion pair of alkyl phosphine and a borane or borate compound.

The repeating unit of Chemical Formula 2a and the photoreactive polymer according to an exemplary embodiment, including the repeating unit may be prepared by above-mentioned method. Further, in the case in which the photoreactive polymer further includes an olefin-, cyclic-olefin- or acrylate-based repeating unit, or the like, the photoreactive polymer may be obtained by forming the repeating unit using a general preparation method of each of the corresponding repeating units, and then, copolymerizing the repeating unit with the repeating unit of Chemical Formula 2a prepared by the above-mentioned method.

On the other hand, in the case in which a photoreactive polymer includes the repeating unit of Chemical Formula 2b, the photoreactive polymer may be prepared by a preparation method according to another exemplary embodiment of the present invention.

The preparation method of a photoreactive polymer according to another exemplary embodiment of the present invention includes: performing a ring-opening polymerization of a norbornenol- or norbornenalkylol-based monomer in the presence of a catalyst composition containing a precatalyst including a transition metal in Group 4, 6 or 8 and a cocatalyst to form a ring-opened polymer; and introducing a photoreactive group represented by the following Chemical Formula 1a in the ring-opened polymer to form a repeating unit represented by the following Chemical Formula 2b.

[Chemical Formula 1a]

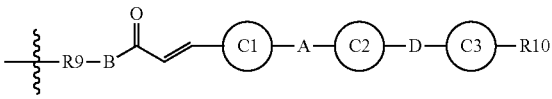

[Chemical Formula 2b]

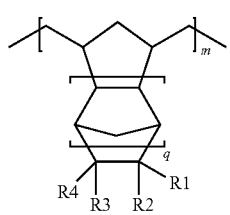

Each symbol in Chemical Formula 1a is as defined above, and each symbol in Chemical formula 2b is as defined above.

In this case, the photoreactive group may be introduced by performing a condensation reaction of the ring-opened polymer with a carboxylic acid compound or acyl chloride compound having a photoreactive group corresponding to Chemical Formula 1a.

As an alternative method, the photoreactive polymer may be prepared by performing a ring-open polymerization of the monomer of Chemical Formula 1 in the presence of a catalyst composition containing a precatalyst including a transition metal in Group 4, 6, or 8 and a cocatalyst to form a repeating unit of Chemical Formula 2b.

In the performing of the ring-opening polymerization reaction, as hydrogen is added to a double bond of a norbornene ring included in the monomer of Chemical Formula 1, or the like, ring-opening may be performed, and polymerization is simultaneously performed, such that the repeating unit of Chemical Formula 2b, or the like, and the photoreactive polymer including the repeating unit may be prepared.

The ring-opening polymerization may be carried out in the presence of a catalyst mixture consisting of a precatalyst including a transition metal in Group 4 (e.g., Ti, Zr, or Hf), Group 6 (e.g., Mo, or W) or Group 8 (e.g., Ru, or Os); a cocatalyst providing a Lewis base capable of forming a weak coordinate bond with the metal of the precatalyst; or optionally a neutral activator in Group 15 or Group 16 capable of improving the activity of the metal of the precatalyst. In the presence of the catalyst mixture as described above, a linear alkene capable of adjusting a molecular weight such as 1-alkene, 2-alkene, or the like, is added in an amount of about 1 to about 100 mol % with respect to the monomer, and a polymerization reaction is carried out at a temperature of about 10 to about 200° C. Then, a catalyst including a transition metal in Group 4 (e.g., Ti, or Zr) or Groups 8 to 10 (e.g., Ru, Ni, or Pd) is added in an amount of about 1 to about 30 wt. % with respect to the monomer to perform a hydrogenation reaction on the double bond of the norbornene ring at about 10 to about 250° C.

A reaction temperature is excessively low, which deteriorates the polymerization activity, and the reaction temperature is excessively high, which results in a cleavage of the catalyst. In addition, a hydrogenation reaction temperature is excessively low, which deteriorates the activity of the hydrogenation reaction, and the hydrogenation reaction temperature is excessively high, which results in a cleavage of the catalyst.

The catalyst mixture includes one mole of a precatalyst including a transition metal in Group 4 (e.g., Ti, Zr, or Hf), Group 6 (e.g., Mo, or W) or Group 8 (e.g., Ru, or Os); and about 1 to about 100,000 moles of a cocatalyst providing a Lewis base capable of forming a weak coordinate bond with the metal of the precatalyst; or and optionally includes about 1 to about 100 moles of an activator including a neutral element in Group 15 or 16 capable of improving the activity of the metal of the precatalyst.

A content of the cocatalyst is less than about one mole, which causes a failure in activation of the catalyst, and the content is greater than about 100,000 moles, which deteriorates the catalyst activity. The activator may be unnecessary depending on the kind of precatalyst. A content of the activator is less than about one mole, which causes a failure in activation of the catalyst, and the content is greater than about 100 moles, which results in a decrease in a molecular weight.

A content of the catalyst including the transition metal in Group 4 (e.g., Ti, or Zr) or Groups 8 to 10 (e.g., Ru, Ni, or Pd) used in the hydrogenation reaction is less than about 1 wt. % with respect to the monomer, which causes a failure in hydrogenation, and the content is greater than about 30 wt. %, which causes discoloration of the polymer.

The precatalyst including a transition metal in Group 4 (e.g., Ti, Zr, or Hf), Group 6 (e.g., Mo, or W) or Group 8 (e.g., Ru, or Os) may refer to a transition metal compound, such as $TiCl_4$, $WCl_6$, $MoCl_5$, $RuCl_3$, or $ZrCl_4$, having a functional group that is readily leaving from the central transition metal by the first cocatalyst providing a Lewis base and participating in a Lewis acid-base reaction to help the central transition metal to be changed into a catalyst active species.

In addition, the examples of the cocatalyst providing a Lewis base capable of forming a weak coordinate bond with the metal of the precatalyst may include borane or borate such as $B(C_6F_5)_3$, or alkylaluminum, alkylaluminum halide or aluminum halide, such as methylaluminoxane (MAO), $Al(C_2H_5)_3$, or $Al(CH_3)Cl_2$. Alternatively, a substituent such as lithium, magnesium, germanium, lead, zinc, tin, silicon, or the like, may be used instead of aluminum. In this manner, the cocatalyst is a compound that readily reacts with a Lewis base to provide vacancies in the transition metal and forms a weak coordinate bond with the transition metal compound in order to stabilize the produced transition metal; or a compound providing such a compound.

Depending on the type of the precatalyst, a polymerization activator may be required or not. The examples of the activator including a neutral element in Group 15 or 16 capable of improving the activity of the metal of the precatalyst may include water, methanol, ethanol, isopropyl alcohol, benzylalcohol, phenol, ethyl mercaptan, 2-chloroethanol, trimethylamine, triethylamine, pyridine, ethylene oxide, benzoyl peroxide, t-butyl peroxide, or the like.

The catalyst including a transition metal in Group 4 (e.g., Ti, or Zr) or Groups 8 to 10 (e.g., Ru, Ni, or Pd) used for the hydrogenation reaction may be prepared as a homogeneous form instantly miscible with a solvent, or as a metal catalyst complex supported on a particulate support. Preferably, the examples of the particulate support may include silica, titania, silica/chromia, silica/chromia/titania, silica/alumina, aluminum phosphate gel, silanized silica, silica hydrogel, montmorillonite clay, or zeolite.

The repeating unit of Chemical Formula 2b and the photoreactive polymer according to an exemplary embodiment, including the repeating unit may be prepared by above-mentioned method. Further, even in the case in which the photoreactive polymer further includes an olefin-, cyclic-olefin- or acrylate-based repeating unit, or the like, the photoreactive polymer may be obtained by forming the repeating unit using a general preparation method of each of the corresponding repeating units, and then, copolymerizing this repeating unit and the repeating unit of Chemical Formula 2b prepared by the above-mentioned method.

Meanwhile, in accordance with another exemplary embodiment of the present invention, there is provided an alignment layer comprising the above-mentioned photoreactive polymer. The alignment layer may include a film type alignment film as well as a thin-film type alignment layer. In accordance with another exemplary embodiment of the present invention, there is provided a liquid crystal retardation film comprising the alignment layer, and a liquid crystal layer on the alignment layer.

The alignment layer and the liquid crystal retardation film may be prepared using constituent components and preparation methods known in the art to which the present invention pertains, excepting for including the above-mentioned photoreactive polymer as a photo-alignment polymer.

For example, the alignment layer may be formed by mixing the photoreactive polymer with a binder resin and a photo-initiator, dissolving the mixture in an organic solvent to obtain a coating composition, coating the coating composition on a substrate, and then curing the coating composition by UV light exposure.

As the binder resin, an acrylate-based compound, more specifically, pentaerythritol triacrylate, dipentaerythritol hexaacrylate, trimethylolpropane triacrylate, tris(2-acryloyloxyethyl) isocyanurate, or the like, may be used.

In addition, as the photo-initiator, any typical photo-initiator known to be applicable to alignment layers may be used without any limitations. For example, the photo-initiator known as product name Irgacure 907 or Irgacure 819 may be used.

In addition, as the organic solvent, toluene, anisole, chlorobenzene, dichloroethane, cyclohexane, cyclopentane, propylene glycol methyl ether acetate, or the like, may be used. Since the above-mentioned photoreactive norbornene-based copolymer has excellent solubility to various organic solvents, other organic solvents may also be used without any limitations.

In the coating composition, a concentration of the solid components including the photoreactive polymer, the binder resin, and the photo-initiator may be in the range of 1 to 15 wt. %, preferably 10 to 15 wt. % for casting the alignment layer in a film form, or 1 to 5 wt. % for casting the alignment layer in a thin film form.

The alignment layer may be formed, for example, on a substrate as shown in FIG. 1, or under the liquid crystal layer to serve to align the liquid crystal. Here, as the substrate, a substrate including a cyclic polymer, a substrate including an acryl polymer, or a substrate including a cellulose polymer, or the like, may be used. The coating composition is coated on the substrate by various methods, such as bar coating, spin coating, blade coating, etc. and then cured under UV light exposure, thereby forming the alignment layer.

The UV light curing may cause photo-alignment, and this step, a polarized UV light in a wavelength range of about 150 to about 450 nm is irradiated, thereby bringing about alignment. Here, an exposure intensity of the light is about 50 mJ/cm$^2$ to about 10 J/cm$^2$, preferably about 500 mJ/cm$^2$ to about 5 J/cm$^2$.

The UV light used herein may be selected from UV light polarized by passing through or being reflected from ① a polarizing device using a transparent substrate such as quartz glass, soda-lime glass, soda-lime-free glass, or the like of which a dielectric anisotropic material is coated on a surface; ② a polarizer finely deposited with aluminum or other metallic wires; or ③ a Brewster polarizer using reflection from quartz glass, or the like.

A substrate temperature during UV light irradiation is preferably room temperature. However, in some case, the UV light may be irradiated in a state in which the substrate is heated in a temperature range of 100° C. or less. Preferably, a final coating layer formed through a series of processes as described above has a layer thickness of about 30 to about 1000 nm.

The liquid crystal retardation film may be prepared by forming the alignment layer by the above-mentioned method and forming the liquid crystal layer thereon according to a general method. As the alignment layer as described above includes the photoreactive polymer, excellent interactions with the liquid crystal molecules may be implemented, and thus, photo-alignment may be effectively performed.

The alignment layer or the liquid crystal retardation film may be applied to optical films or filters used to implement stereoscopic images.

In accordance with another exemplary embodiment, there is provided a display device including the alignment layer. The display device may be a liquid crystal display device including the alignment layer for liquid crystal alignment; or a stereoscopic imaging display device in which the alignment layer is included in an optical film or filter for implementing stereoscopic images, or the like. However, since constituent components of the display device are the same as those of a typical display device, except for including the above-mentioned photoreactive polymer and the alignment layer, a detailed description thereof will be omitted.

Hereinafter, preferred Examples of the present invention will be provided for better understanding of the present invention. It is to be understood that the following Examples are only for illustrative purposes and are not intended to limit the scope of the present invention.

In following Examples, all the works dealing with compounds susceptible to air or water were carried out using standard Schlenk techniques or dry-box techniques. The nuclear magnetic resonance (NMR) spectra were acquired using a Bruker 300 spectrometer, where $^1$H NMR and $^{13}$C NMR measurements were conducted at 300 MHz and 75 MHz, respectively. The molecular weight and the molecular weight distribution of the polymer obtained by ring-opening hydrogenation were measured using gel permeation chromatography (GPC), which employed a polystyrene sample as a reference.

For purification, toluene was distilled in potassium/benzophenone, and dichloromethane was distilled in CaH$_2$.

EXAMPLE

Preparation of Cyclic Olefin Compound

Example 1

Preparation of (E)-bicyclo[2.2.1]hept-5-en-2-ylmethyl 3-(4-(4'-propylbi(cyclohexan)-4-yl)phenyl)acrylate In a flask were placed (E)- 3-(4-(4-'-propylbi(cyclohexan)-4-yl) phenyl)acrylic acid (100.0 g, 0.28mol, Fw=354.53), N-(3-dimethylaminopropyl)-N'-ethylcarbodiimide hydrochloride (EDCI, 87.6 g, 0.56 mol), and N,N-dimethylamidopyridine (DMAP, 68.42 g, 0.56 mol), and CH$_2$Cl$_2$ ( 1000 ml) was added thereto. 5-Norbornene-2-methanol (34.77 g, 0.28 mol, Fw=124.18) was added thereto, and stirred at room temperature for 20 hours. After the reaction was completed, water was added thereto, and the organic phase was extracted from water. Then, the organic phase was washed with saline water. The organic phase was dried over magnesium sulfate, filtered, and purified by column chromatography (EA:Hex=1:7), thereby obtaining 72.3 g of the title compound (yield: 56%, Fw=460.69, purity (GC): 98%).

NMR(CDCl$_3$ (500 MHz), ppm): 0.90 (3, t), 1.25~1.86 (27, m), 2.13 (1, quin), 2.27 (1, m), 2.58 (1, m), 2.72 (1, quin), 4.25 (1, dd), 4.50 (1, dd), 6.05 (2, q), 6.31 (1, d), 7.25 (2, d), 7.48 (1, d), 7.63 (2, d)

Example 2

Preparation of (E)-(bicyclo[2.2.1]hept-5-en-2-ylmethyl) 3-(4-(5-(4-propylcyclohexyl)-1,3-dioxan-2-yl)phenyl)acrylate In a flask were placed (E)-3-(4-(5-(4-propylcyclohexyl)-1,3-dioxan-2-yl)phenyl)acrylic acid (100 g, 0.28 mol, Fw=358.47), N-(3-dimethylaminopropyl)-N'-ethylcarbodiimide hydrochloride (EDCl, 87.6 g, 0.56 mol), and N,N-dimethylamidopyridine (DMAP, 10.5 g, 0.56 mol), and CH$_2$Cl$_2$ (1000 ml) was added thereto. 5-Norbornene-2-methanol (34.77 g, 0.28 mol, Fw=124.18) was added thereto, and stirred at room temperature for 20 hours. After the reaction was completed, water was added thereto, and the organic phase was extracted from water. Then, the organic phase was washed with saline water. The organic phase was dried over magnesium sulfate, filtered, and purified by column chromatography (EA:Hex=1:7), thereby obtaining 67.7 g of the title compound (yield: 52%, Fw=464.64, purity (GC): 98%).

NMR(CDCl$_3$ (500 MHz), ppm): 0.90 (3, t), 1.25~1.75 (19, m), 2.13 (1, sex), 2.27 (1, m), 2.58 (1, m), 3.63 (2, dd), 3.88 (2, dd), 4.25 (1, dd), 4.50 (1, dd), 5.98 (1, s), 6.05 (2, q), 6.31 (1, d), 7.42 (2, d), 7.48 (1, d), 7.64 (2, d)

Example 3

Preparation of (E)-(bicyclo[2.2.1]hept-5-en-2-ylmethyl) 3-(4'-(4-propylcyclohexyl)biphenyl-4-yl)acrylate In a flask were placed a (E)-3-(4'-(4-propylcyclohexyl) biphenyl-4-yl)acrylic acid (25 g, 71.7 mmol, Fw=348.48), 5-norbornene-2-methanol (8.90 g, 71.7 mmol, Fw=124.18), zirconium acetate hydroxide (0.25 g, 1 wt. %), and xylene (60 ml), and then, azeotropic reflux was conducted at 180° C. in the nitrogen atmosphere for about 24 hours. After reaction, a temperature was lowered to room temperature and 100 vol. % of ethyl acetate was added thereto. The organic phase was extracted with 1 M HCl and washed with water once more. The organic phase was dried over magnesium sulfate, followed by removal of the solvent. The resultant was purified by column chromatography (EA: Hex=1:10), thereby obtaining 21.19 g of the title compound (yield: 65%, Fw=454.64, purity (GC): 98%).

NMR(CDCl$_3$ (500 MHz), ppm): 0.90 (3, t), 1.50~1.86 (17, m), 2.13 (1, sex), 2.27 (1, m), 2.58 (1, m), 2.72 (1, quin), 4.25 (1, dd), 4.50 (1, dd), 6.05 (2, q), 6.31 (1, d), 7.36 (2, s), 7.37 (2, d), 7.44 (2, d), 7.48 (1, s), 7.59 (2, d)

Example 4

Preparation of (E)-3-((bicyclo[2.2.1]hept-5-en-2-yl) propyl) 3-(4-(4'-propylbi(cyclohexan)-4-yl)phenyl) acrylate In a flask were placed (E)-3-(4-(4'-propylbi(cyclohexan)-4-yl)phenyl)acrylic acid (25 g, 70.5 mmol, Fw=354.53), 5-norbornene-2-propanol (10.7 g, 70.5 mmol, Fw=152.24), zirconium acetate hydroxide (0.25 g, 1 wt. %), and xylene (30 ml), and then, azeotropic reflux was conducted at 180° C. in the nitrogen atmosphere for about 24 hours. After reaction, a temperature was lowered to room temperature and 100 vol. % of ethyl acetate was added thereto. The organic phase was extracted with 1 M HCl and washed with water once more. The organic phase was dried over magnesium sulfate, and the solvent was removed, followed by purification through column chromatography (EA:Hex=1: 10), thereby obtaining 24.46 g of the title compound (yield: 71%, Fw=488.74, purity (GC): 98%).

NMR(CDCl$_3$ (500 MHz), ppm): 0.90 (3, t), 1.25~1.86 (22, m), 2.27 (1, m), 2.58 (1, m), 2.72 (1, quin), 4.15 (2, t), 6.05 (2, q), 6.31 (1, d), 7.36 (2, s), 7.37 (2, d), 7.44 (2, d), 7.48 (1, s), 7.59 (1, d)

Example 5

Polymerization of (E)-bicyclo[2.2.1]hept-5-en-2-ylmethyl 3-(4-(4'-propylbi(cyclohexan)-4-yl)phenyl) acrylate In a 250 ml Schlenk flask were placed the compound (50 mmol) prepared in Example 1 as a monomer, and 400 wt. % of purified toluene as a solvent, and 10 mol % of 1-octene was added thereto. The mixture was heated to 90° C. while being stirred, and Pd(OAc)$_2$ (16 umol) and tricyclohexylphosphine (32 umol) dissolved in 1 ml of dichloromethane as a catalyst and dimethylanilinium tetrakis(pentafluorophenyl)borate (32 umol) as a cocatalyst were added thereto. The mixture was stirred at 90° C. for 16 hours, thereby performing a reaction.

After the reaction, the reactant was put in an excess of ethanol to obtain a white polymer precipitate. The precipitate was filtered through a glass funnel to collect a polymer, and the collected polymer was dried in a vacuum oven at 60° C. for 24 hours, thereby obtaining a polymer (Mw=189,000, PDI=2.59, yield=54%), Example 6 polymerization of (E)-(bicyclo[2.2.1]hept-5-en-2-ylmethyl) 3-(4-(5-(4-propylcyclohexyl)-1,3-dioxan-2-yl)phenyl)acrylate In a 250 ml Schlenk flask were placed the compound (50 mmol) prepared in Example 2 as a monomer, and 400 wt. % of purified toluene as a solvent, and 10 mol % of 1-octene was added thereto. The mixture was heated to 90° C. while being stirred, and Pd(OAc)$_2$ (16 umol) and tricyclohexylphosphine (32 umol) dissolved in 1 ml of dichloromethane as a catalyst and dimethylanilinium tetrakis(pentafluorophenyl)borate (32 umol) as a cocatalyst were added thereto. The mixture was stirred at 90° C. for 16 hours, thereby performing a reaction.

After the reaction, the reactant was put in an excess of ethanol to obtain a white polymer precipitate. The precipitate was filtered through a glass funnel to collect a polymer, and the collected polymer was dried in a vacuum oven at 60° C. for 24 hours, thereby obtaining a polymer (Mw=175,000, PDI=2.97, yield=59%).

Example 7 polymerization of (E)-(bicyclo[2.2.1]hept-5-en-2-ylmethyl) 3-(4'-(4-propylcyclohexyl)biphenyl-4-yl) acrylate In a 250 ml Schlenk flask were placed the compound (50 mmol) prepared in Example 3 as a monomer, and 400 wt. % of purified toluene as a solvent, and 10 mol % of 1-octene was added thereto. The mixture was heated to 90° C. while being stirred, and Pd(OAc)$_2$ (16 umol) and tricyclohexylphosphine (32 umol) dissolved in 1 ml of dichloromethane as a catalyst and dimethylanilinium tetrakis(pentafluorophenyl)borate (32 umol) as a cocatalyst were added thereto. The mixture was stirred at 90° C. for 16 hours, thereby performing a reaction.

After the reaction, the reactant was put in an excess of ethanol to obtain a white polymer precipitate. The precipitate was filtered through a glass funnel to collect a polymer, and the collected polymer was dried in a vacuum oven at 60° C. for 24 hours, thereby obtaining a polymer (Mw=181,000, PDI=3.23, yield=52%).

Example 8

Polymerization of (E)-3-((bicyclo[2.2.1]hept-5-en-2-yl)propyl) 3-(4-(4'-propylbi(cyclohexan)-4-yl)phenyl)acrylate In a 250 ml Schlenk flask were placed the compound (50 mmol) prepared in Example 4 as a monomer, and 400 wt. % of purified toluene as a solvent, and 10 mol % of 1-octene was added thereto. The mixture was heated to 90° C. while being stirred, and Pd(OAc)$_2$ (16 umol) and tricyclohexylphosphine (32 umol) dissolved in 1 ml of dichloromethane as a catalyst and dimethylanilinium tetrakis(pentafluorophenyl)borate (32 umol) as a cocatalyst were added thereto. The mixture was stirred at 90° C. for 16 hours, thereby performing a reaction.

After the reaction, the reactant was put in an excess of ethanol to obtain a white polymer precipitate. The precipitate was filtered through a glass funnel to collect a polymer, and the collected polymer was dried in a vacuum oven at 60° C. for 24 hours, thereby obtaining a polymer (Mw=163,000, PDI=2.74, yield=62%).

Example 9

Preparation of Photoreactive Polymer by Ring-Opening Polymerization and Hydrogenation Reaction In a 250 ml Schlenk flask in the Ar atmosphere was placed 5-norbornene-2-methanol (6.20 g, 50 mmol), and then purified toluene (34 g) was added thereto as a solvent. With the flask maintained at a polymerization temperature of 80° C., first, triethyl aluminum (11.4 mg, 1.0 mmol) was added thereto as a cocatalyst. Subsequently, 0.01 M (mol/L) toluene solution (1 ml (WCl$_8$: 0.01 mmol, ethanol: 0.03 mmol) containing a mixture of tungsten hexachloride (WCl$_6$) and ethanol at a mixing ratio of 1:3 was added thereto. Finally, 1-octene (0.84 g, 7.5 mmol) as a molecular weight modifier was added to the flask, and then the mixture was stirred at 80° C. for 18 hours, thereby performing a reaction. After the reaction was completed, a small amount of ethyl vinyl ether as a polymerization inhibitor was added dropwise to the polymerization solution, and the flask was stirred for 5 minutes.

After transferring the polymerization solution to a 300 mL high-pressure reactor, triethyl aluminum (TEA, 0.06 ml) was added thereto. Subsequently, grace raney nickel (0.50 g, slurry phase in water) was added thereto, and the polymerization solution was stirred at 150° C. for 2 hours under the hydrogen pressure maintained at 80 atm, thereby performing a reaction. After the reaction was completed, the polymerization solution was added dropwise to acetone to cause precipitation. Thereafter, the obtained precipitate was filtered and dried in a vacuum oven at 70° C. for 15 hours. As a result, 5.62 g of a ring-opened hydrogenated polymer of 5-norbornene-2-methanol was obtained (yield=90.6%, Mw=69,900, PDI=4.92).

In a 250 ml two-neck flask were placed the ring-opened hydrogenated polymer of 5-norbornene-2-methanol (15 g, 0.121 mol), triethylamine (Aldrich, 61.2 g, 0.605 mol), and THF (50 ml), and then, the mixture was stirred in an ice-water bath at 0° C.

(E)-3-(4-(4'-propylbi(cyclohexan)-4-yl)phenyl)acryloyl chloride (49.61 g, 0.133 mol, Fw=372.97) was dissolved in THF (60 ml) and slowly added using an additional flask. After 10 minutes, the reactant was warmed to room temperature and stirred for 18 more hours. The solution was diluted with ethyl acetate, transferred to a separatory funnel, and washed with water and NaHCO$_3$ several times. The reaction solution was added dropwise to acetone to cause precipitation, and the resultant precipitate was filtered and dried in a vacuum oven at 70° C. for 15 hours. As a result, a ring-opened hydrogenated polymer of the monomer in Example 1 was prepared (yield: 92%).

Comparative Example 1

Synthesis of (E)-Phenyl-4-(3-(3-(bicycle[2.2.1]hept-5-en-2-yl)propoxy)-3-oxoprop-1-en-1-yl)benzoate In a flask were placed (E)-3-(4-(phenoxycarbonyl)phenyl) acrylic acid (9.15 g, 34.1 mmol, Fw=268.27), 5-norbornene-2-propanol (10.7 g, 70.5 mmol, Fw=152.24), zirconium acetate hydroxide (0.25 g, 1 wt. %), and xylene (30 ml), and then, azeotropic reflux was conducted at 180° C. in the nitrogen atmosphere for about 24 hours. After reaction, a temperature was lowered to room temperature and 100 vol. % of ethyl acetate was added thereto. The organic phase was extracted with 1 M HCl and washed with water once more. The organic phase was dried over magnesium sulfate, and the solvent was removed, followed by purification through column chromatography (EA:Hex=1:10), thereby obtaining 9.47 g of the title compound (yield: 69%, Fw=402.49, purity (GC): 97.5%).

NMR(CDCl$_3$ (300 MHz), ppm): 0.59 (m, 1), 1.48~1.16 (m, 2), 1.91~1.83 (m, 1), 2.45 (m, 1), 2.94~2.75 (m, 2), 5.0~4.9 (m, 2), 6.17~5.98 (m, 2), 6.55 (d, 1), 7.23~7.14 (m, 2), 7.35 (d, 2), 7.84~7.71 (m, 5)

Comparative Example 2

Polymerization of (E)-Phenyl-4-(3-(3-(bicycle[2.2.1]hept-5-en-2-yl)propoxy)-3-oxoprop-1-en-1-yl)benzoate In a 250 ml Schlenk flask were placed the compound (3 mmol) prepared in Comparative Example 1 as a nomomer and purified toluene (3 ml) as a solvent. The mixture was heated to 90° C. while being stirred, and Pd(OAc)$_2$ (16 umol) and tricyclohexylphosphine (32 umol) dissolved in 1 ml of dichloromethane as a catalyst and dimethylanilinium tetrakis(pentafluorophenyl)borate (32 umol) as a cocatalyst were added thereto. The mixture was stirred at 90° C. for 18 hours, thereby performing a reaction.

After the reaction, the reactant was put in an excess of ethanol to obtain a yellow polymer precipitate. The precipitate was filtered through a glass funnel to collect a polymer, and the collected polymer was dried in a vacuum oven at 60° C. for 24 hours, thereby obtaining 1.01 of a polymer (Mw=143,000, PDI=3.4, yield=84%).

Manufacturing of Alignment Layer and Retardation Film 3 wt. % of the photoreactive polymers according to Examples 5 to 9 and Comparative Example 2, 1.0 wt. % of an acrylate based binder (PETA), and 0.5 wt. % of a photoinitiator (Irgacure 907 manufactured by Ciba-Geigy Chemical Corp.) were dissolved in a toluene solvent, respectively, and these solvents were dropped and bar-coated on a COP film, respectively.

After drying the COP film at 80° C. for 2 minutes, polarized UV light (100 mW/cm$^2$) was irradiated thereon. The exposure was conducted using a wire-grid polarizer (Moxtek Inc.) with a high-pressure mercury lamp having an intensity of 100 mW/cm$^2$ as a light source so that UV light vertically polarized with respect to a film advancing direction was irradiated. Light intensity of the polarized UV light was adjusted by time.

A-plate liquid crystals (manufactured by Merck, 25 wt. % toluene solution) were dropped and bar-coated on the alignment layer, and UV light (15 mJ/cm$^2$) was irradiated thereon, followed by curing the liquid crystals, thereby obtaining a retardation film.

Experimental Example

Evaluation of Alignment Property

Each of the retardation films manufactured using the photoreactive polymer of Examples 5 and 6 and Comparative Example 2 was observed between two vertically arranged polarizers using a polarized microscope, thereby evaluating the alignment property.

That is, the retardation film was disposed between two vertically arranged polarizers based on a COP film (manufacturer: Zeon, product name: Zeonor) having a thickness of 100 μm, and the polarized microscope was used to determine the transmittance of an incident light passing through the polarizers and the retardation film, thereby measuring a degree of light leakage. In this case, the degree of light leakage was evaluated based on a 10-point scale.

In addition, a quantitative phase difference value of the retardation film was measured using an Axoscan (Axomatrix). In this case, a phase difference value in a film surface direction was measured using light having a wavelength of 550 nm.

TABLE 1

|  | Alignment Property | Phase Difference Value |
|---|---|---|
| Example 5 | 10 | 130 nm |
| Example 6 | 10 | 129 nm |
| Example 8 | 10 | 130 nm |
| Comparative Example 2 | 8 | 113 nm |

Referring to Table 1, in the retardation films manufactured using the polymers of Examples, a liquid crystal alignment direction was uniform irrespective of a wavelength of the incident light, such that the retardation films had a good alignment property, and in-film phase difference values thereof were entirely about 130 nm, such that it may be confirmed that excellent anisotropic properties by liquid crystals was implemented.

On the contrary, in the retardation film manufactured using the polymer of Comparative Example 2, the alignment property was deteriorated, and a liquid crystal alignment direction was not uniform, such that it may be confirmed that light leakage occurred. In addition, in spite of the same liquid crystal thickness, the phase difference value was low (about 113 nm), such that it may be confirmed that anisotropic properties were not suitably implemented.

The invention claimed is:

1. A cyclic olefin compound having a photoreactive group represented by the following Chemical Formula 1:

[Chemical Formula 1]

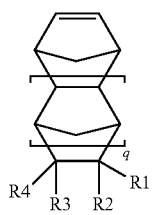

in Chemical Formula 1, q is an integer from 0 to 4;

at least one of R1, R2, R3, and R4 is a radical represented by the following Chemical Formula 1a, among R1 to R4, the remainders other than the radical of Chemical Formula 1a are the same as or different from one another and each independently selected from the group consisting of hydrogen; halogen; substituted or unsubstituted linear or branched alkyl having 1 to 20 carbon atoms; substituted or unsubstituted linear or branched alkenyl having 2 to 20 carbon atoms; substituted or unsubstituted linear or branched alkynyl having 2 to 20 carbon atoms; substituted or unsubstituted cycloalkyl having 3 to 12 carbon atoms; substituted or unsubstituted aryl having 6 to 40 carbon atoms; substituted or unsubstituted arylalkyl having 5 to 12 carbon atoms; and a polar functional group including at least one selected from oxygen, nitrogen, phosphorus, sulfur, silicon, and boron, when R1 to R4 are not hydrogen, halogen, or a polar functional group, at least one combination of R1 and R2 or R3 and R4 is bonded to each other to form an alkylidene group having 1 to 10 carbon atoms, or R1 or R2 is bonded to either R3 or R4 to form a saturated or unsaturated aliphatic ring having 4 to 12 carbon atoms or an aromatic ring having 6 to 24 carbon atoms,

[Chemical Formula 1a]

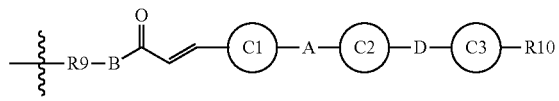

in Chemical Formula 1a,

A is selected from the group consisting of a single bond, substituted or unsubstituted alkylene having 1 to 20 carbon atoms, substituted or unsubstituted alkenylene having 2 to 20 carbon atoms, substituted or unsubstituted cycloalkylene having 3 to 12 carbon atoms, substituted or unsubstituted arylene having 6 to 40 carbon atoms, substituted or unsubstituted arylalkylene having 7 to 15 carbon atoms, and substituted or unsubstituted alkynylene having 2 to 20 carbon atoms, B is a single bond, oxygen, sulfur, —NH—, or 1,4-phenylene, R9 is selected from the group consisting of a single bond, substituted or unsubstituted alkylene having 1 to 20 carbon atoms, substituted or unsubstituted alkenylene having 2 to 20 carbon atoms, substituted or unsubstituted cycloalkylene having 3 to 12 carbon atoms, substituted or unsubstituted arylene having 6 to 40 carbon atoms, substituted or unsubstituted arylalkylene having 7 to 15 carbon atoms, and substituted or unsubstituted alkynylene having 2 to 20 carbon atoms, C1 is C6-C40 arylene unsubstituted or substituted with at least one functional group selected from the group consisting of halogen, cyano, and nitro; C7-C15 arylalkylene unsubstituted or substituted with at least one functional group selected from halogen, cyano, and nitro; or C4-C40 heteroarylene including a hetero element in Group 14, 15 or 16, C2 is C6-C40 arylene unsubstituted or substituted with at least one functional group selected from the group consisting of halogen, cyano, and nitro; C4-C40 heteroarylene including a hetero element in Group 14, 15 or 16; C5-C10 cycloalkylene; or C4-C40 heterocycloalkylene including a hetero element in Group 14, 15, or 16, C3 is C5-C10 cycloalkylene unsubstituted or substituted with at least one functional group selected from the group consisting of halogen, cyano, and nitro, or C4-C40 heterocycloalkylene including a hetero element in Group 14, 15, or 16, D is selected from the group consisting of a single bond, substituted or unsubstituted alkylene having 1 to 20 carbon atoms, substituted or unsubstituted alkenylene having 2 to 20 carbon atoms, substituted or unsubstituted cycloalkylene having 3 to 12 carbon atoms, substituted or unsubstituted arylene having 6 to 40 carbon atoms, substituted or unsubstituted arylalkylene having 7 to 15 carbon atoms, and substituted or unsubstituted alkynylene having 2 to 20 carbon atoms, and R10 is selected from the group consisting of hydrogen; halogen; cyano; nitro; —NCS; substituted or unsubstituted linear or branched alkyl having 1 to 20 carbon atoms; substituted or unsubstituted alkoxy having 1 to 20 carbon atoms; and substituted or unsubstituted aryloxy having 6 to 30 carbon atoms.

2. The cyclic olefin compound of claim 1, wherein the polar functional group including at least one selected from oxygen, nitrogen, phosphorus, sulfur, silicon, and boron is selected from the group consisting of the following functional groups:

—$OR_6$, —$OC(O)OR_6$, —$R_5OC(O)OR_6$, —$C(O)OR_6$, —$R_5C(O)OR_6$, —$C(O)R_6$, —$R_5C(O)R_6$, —$OC(O)R_6$, —$R_5OC(O)R_6$, —$(R_5O)_p$—$OR_6$, —$(OR_5)_p$—$OR_6$, —$C(O)$—$O$—$C(O)R_6$, —$R_5C(O)$—$O$—$C(O)R_6$, —$SR_6$, —$R_5SR_6$, —$SSR_6$, —$R_5SSR_6$, —$S(\!=\!O)R_6$, —$R_5S(\!=\!O)R_6$, —$R_5C(\!=\!S)R_6$—, —$R_5C(\!=\!S)SR_6$, —$R_5SO_3R_6$, —$SO_3R_6$, —$R_5N\!=\!C\!=\!S$, —$N\!=\!C\!=\!S$, —NCO, —$R_5$—NCO, —CN, —$R_5$CN, —$NNC(\!=\!S)R_6$, —$R_5NNC(\!=\!S)R_6$, —$NO_2$, —$R_5NO_2$,

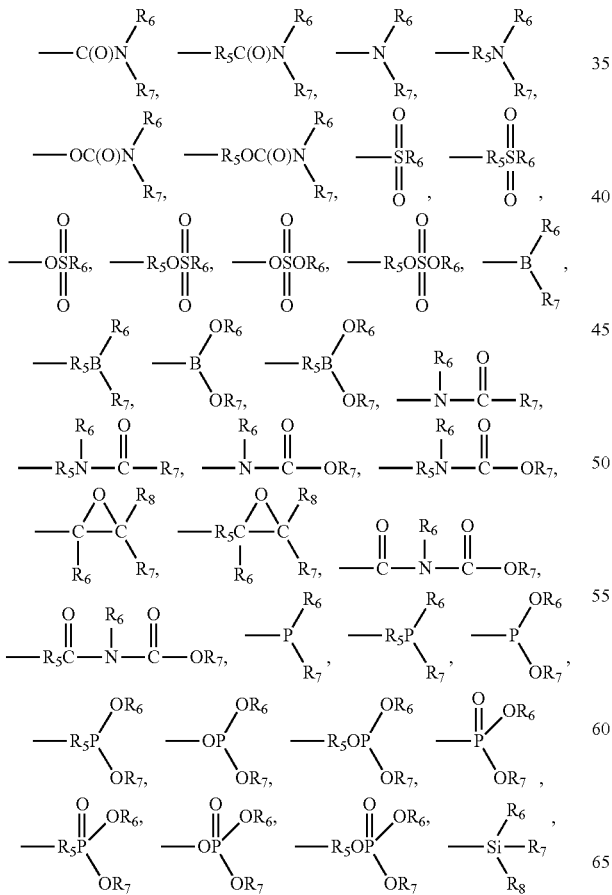

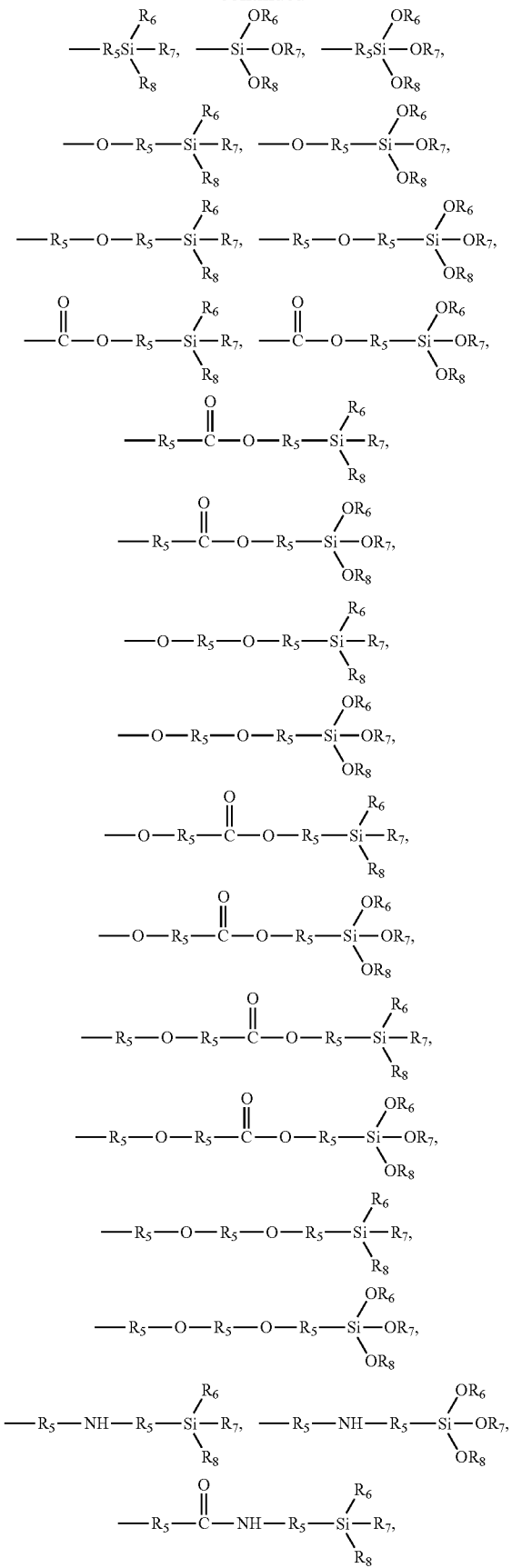

-continued

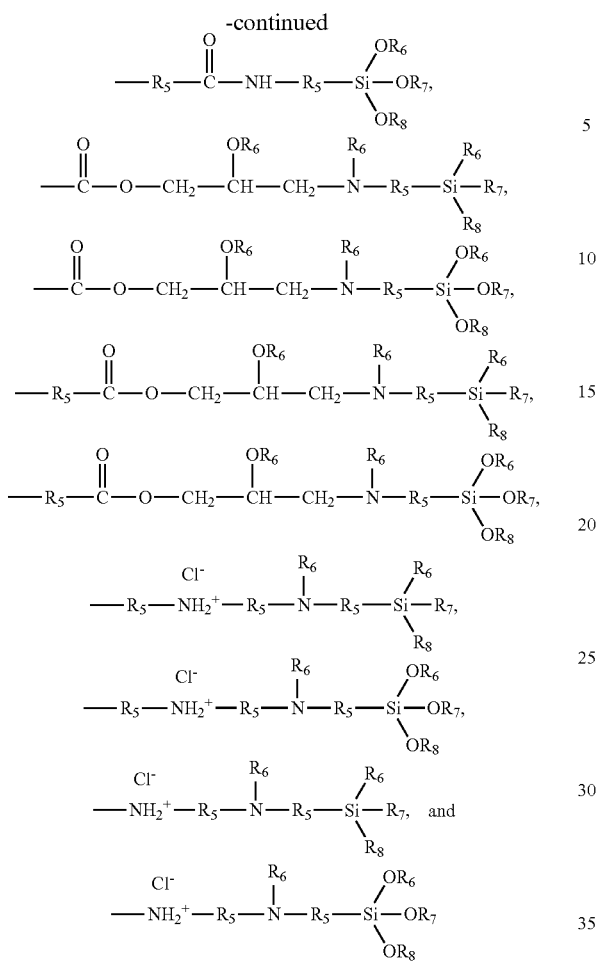

in the polar functional groups, each p is independently an integer from 1 to 10, $R_5$ is substituted or unsubstituted linear or branched alkylene having 1 to 20 carbon atoms; substituted or unsubstituted linear or branched alkenylene having 2 to 20 carbon atoms; substituted or unsubstituted linear or branched alkynylene having 2 to 20 carbon atoms; substituted or unsubstituted cycloalkylene having 3 to 12 carbon atoms; substituted or unsubstituted arylene having 6 to 40 carbon atoms; substituted or unsubstituted carbonyloxylene having 1 to 20 carbon atoms; or substituted or unsubstituted alkoxylene having 1 to 20 carbon atoms; and $R_6$, $R_7$, and $R_8$ are each independently selected from the group consisting of hydrogen; halogen; substituted or unsubstituted linear or branched alkyl having 1 to 20 carbon atoms; substituted or unsubstituted linear or branched alkenyl having 2 to 20 carbon atoms; substituted or unsubstituted linear or branched alkynyl having 2 to 20 carbon atoms; substituted or unsubstituted cycloalkyl having 3 to 12 carbon atoms; substituted or unsubstituted aryl having 6 to 40 carbon atoms; substituted or unsubstituted alkoxy having 1 to 20 carbon atoms; and substituted or unsubstituted carbonyloxy having 1 to 20 carbon atoms.

3. The cyclic olefin compound of claim 2, wherein each functional group of R5 to R8 is unsubstituted or substituted with a functional group selected from the group consisting of halogen, alkyl, alkenyl, alkynyl, haloalkyl, haloalkenyl, haloalkynyl, aryl, haloaryl, arylalkyl, haloarylalkyl, alkoxy, haloalkoxy, carbonyloxy, halocarbonyloxy, aryloxy, haloaryloxy, silyl, and siloxy.

4. A photoreactive polymer comprising a repeating unit represented by the following Chemical Formula 2a or 2b:

[Chemical Formula 2a]

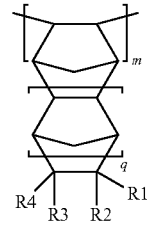

[Chemical Formula 2b]

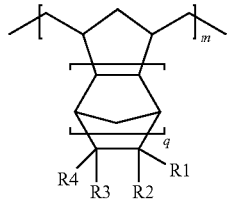

in Chemical Formulas 2a and 2b, each independently,
m is 50 to 5000,
q is an integer from 0 to 4;
at least one of R1, R2, R3, and R4 is a radical represented by the following Chemical Formula 1a,
among R1 to R4, the remainders other than the radical of Chemical Formula 1a are the same as or different from one another and each independently selected from the group consisting of hydrogen; halogen; substituted or unsubstituted linear or branched alkyl having 1 to 20 carbon atoms; substituted or unsubstituted linear or branched alkenyl having 2 to 20 carbon atoms; substituted or unsubstituted linear or branched alkynyl having 2 to 20 carbon atoms; substituted or unsubstituted cycloalkyl having 3 to 12 carbon atoms; substituted or unsubstituted aryl having 6 to 40 carbon atoms; substituted or unsubstituted arylalkyl having 5 to 12 carbon atoms; and a polar functional group including at least one selected from oxygen, nitrogen, phosphorus, sulfur, silicon, and boron,
when R1 to R4 are not hydrogen, halogen, or a polar functional group, at least one combination of R1 and R2 or R3 and R4 is bonded to each other to form an alkylidene group having 1 to 10 carbon atoms, or R1 or R2 is bonded to either R3 or R4 to form a saturated or unsaturated aliphatic ring having 4 to 12 carbon atoms or an aromatic ring having 6 to 24 carbon atoms,

[Chemical Formula 1a]

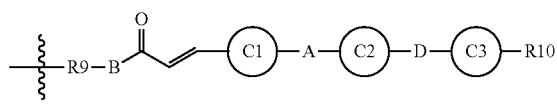

in Chemical Formula 1a,
A is selected from the group consisting of a single bond, substituted or unsubstituted alkylene having 1 to 20 carbon atoms, substituted or unsubstituted alkenylene having 2 to 20 carbon atoms, substituted or unsubstituted cycloalkylene having 3 to 12 carbon atoms, substituted or unsubstituted arylene having 6 to 40 carbon atoms, substituted or unsubstituted arylalkylene having 7 to 15 carbon atoms, and substituted or unsubstituted alkynylene having 2 to 20 carbon atoms, B is a single bond, oxygen, sulfur, —NH—, or 1,4-phenylene, R9 is selected from the group consisting of a single bond, substituted or unsubstituted alkylene having 1 to 20 carbon atoms, substituted or unsubstituted alkenylene having 2 to 20 carbon atoms, substituted or unsubstituted cycloalkylene having 3 to 12 carbon atoms, substituted or unsubstituted arylene having 6 to 40 carbon atoms, substituted or unsubstituted arylalkylene having 7 to 15 carbon atoms, and substituted or unsubstituted alkynylene having 2 to 20 carbon atoms, C1 is C6-C40 arylene unsubstituted or substituted with at least one functional group selected from the group consisting of halogen, cyano, and nitro; C7-C15 arylalkylene unsubstituted or substituted with at least one functional group selected from halogen, cyano, and nitro; or C4-C40 heteroarylene including a hetero element in Group 14, 15 or 16, C2 is C6-C40 arylene unsubstituted or substituted with at least one functional group selected from the group consisting of halogen, cyano, and nitro; C4-C40 heteroarylene including a hetero element in Group 14, 15 or 16; C5-C10 cycloalkylene; or C4-C40 heterocycloalkylene including a hetero element in Group 14, 15, or 16, C3 is C5-C10 cycloalkylene unsubstituted or substituted with at least one functional group selected from the group consisting of halogen, cyano, and nitro, or C4-C40 heterocycloalkylene including a hetero element in Group 14, 15, or 16, D is selected from the group consisting of a single bond, substituted or unsubstituted alkylene having 1 to 20 carbon atoms, substituted or unsubstituted alkenylene having 2 to 20 carbon atoms, substituted or unsubstituted cycloalkylene having 3 to 12 carbon atoms, substituted or unsubstituted arylene having 6 to 40 carbon atoms, substituted or unsubstituted arylalkylene having 7 to 15 carbon atoms, and substituted or unsubstituted alkynylene having 2 to 20 carbon atoms, and R10 is selected from the group consisting of hydrogen; halogen; cyano; nitro; —NCS; substituted or unsubstituted linear or branched alkyl having 1 to 20 carbon atoms; substituted or unsubstituted alkoxy having 1 to 20 carbon atoms; and substituted or unsubstituted aryloxy having 6 to 30 carbon atoms.

5. The photoreactive polymer of claim 4, wherein the photoreactive polymer has a weight average molecular weight of 10,000 to 1,000,000 g/mol.

6. The photoreactive polymer of claim 4, wherein the polar functional group including at least one selected from oxygen, nitrogen, phosphorus, sulfur, silicon, and boron is selected from the group consisting of the following functional groups:

—OR$_6$, —OC(O)OR$_6$, —R$_5$OC(O)OR$_6$, —C(O)OR$_6$, —R$_5$C(O)OR$_6$, —C(O)R$_6$, —R$_5$C(O)R$_6$, —OC(O)R$_6$, —R$_5$OC(O)R$_6$, —(R$_5$O)$_p$—OR$_6$, —(OR$_5$)$_p$—OR$_6$, —C(O)—O—C(O)R$_6$, —R$_5$C(O)—O—C(O)R$_6$, —SR$_6$, —R$_5$SR$_6$, —SSR$_6$, —R$_5$SSR$_6$, —S(═O)R$_6$, —R$_5$S(═O)R$_6$, —R$_5$C(═S)R$_6$—, —R$_5$C(═S)SR$_6$, —R$_5$SO$_3$R$_6$, —SO$_3$R$_6$, —R$_5$N═C═S, —N═C═S, —NCO, —R$_5$—NCO, —CN, —R$_5$CN, —NNC(═S)R$_6$, —R$_5$NNC(═S)R$_6$, —NO$_2$, —R$_5$NO$_2$,

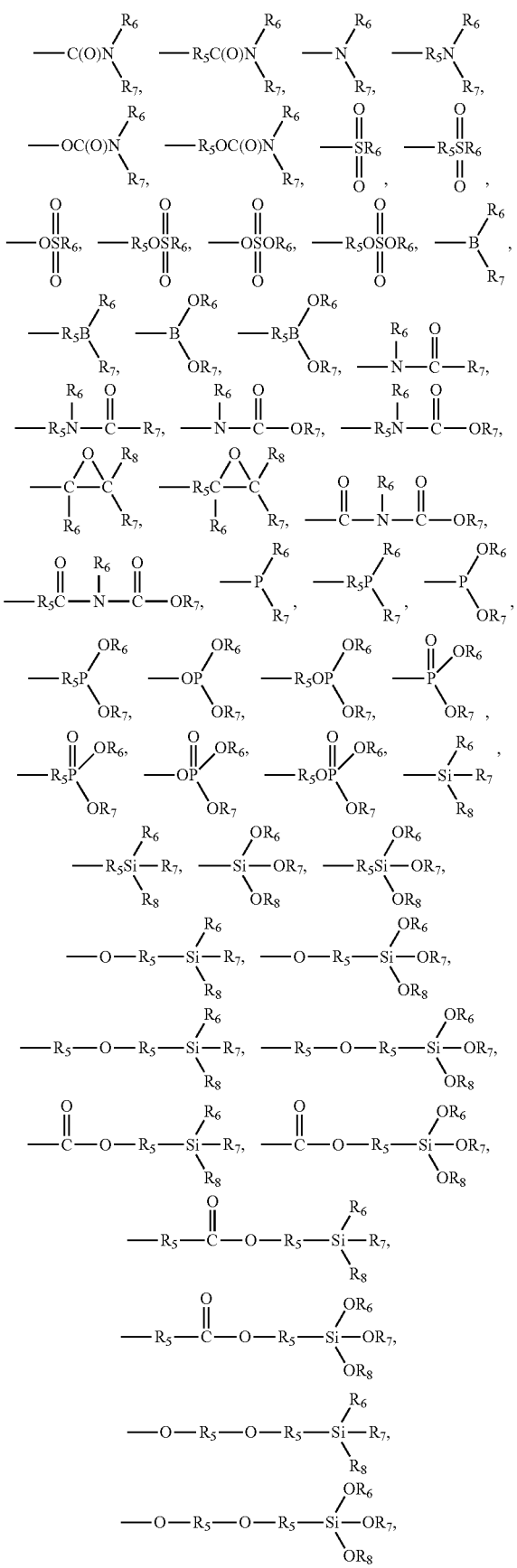

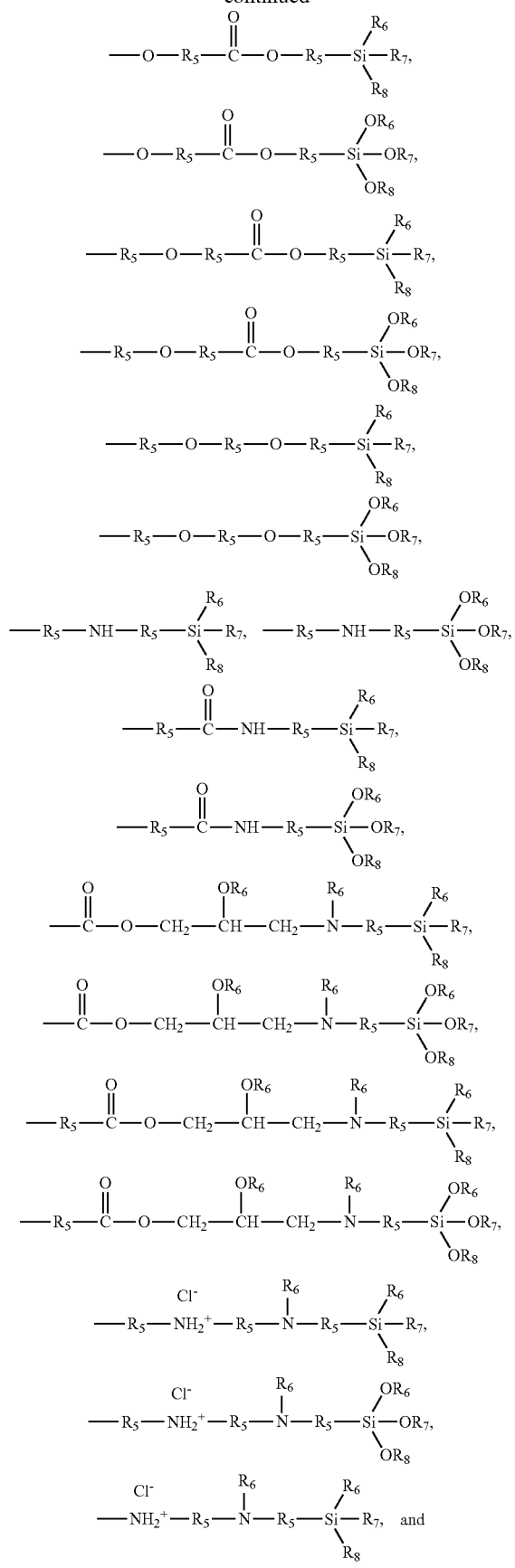

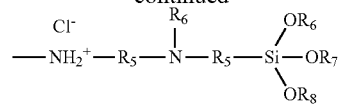

in the polar functional groups, each p is independently an integer from 1 to 10, $R_5$ is substituted or unsubstituted linear or branched alkylene having 1 to 20 carbon atoms; substituted or unsubstituted linear or branched alkenylene having 2 to 20 carbon atoms; substituted or unsubstituted linear or branched alkynylene having 2 to 20 carbon atoms; substituted or unsubstituted cycloalkylene having 3 to 12 carbon atoms; substituted or unsubstituted arylene having 6 to 40 carbon atoms; substituted or unsubstituted carbonyloxylene having 1 to 20 carbon atoms; or substituted or unsubstituted alkoxylene having 1 to 20 carbon atoms; and $R_6$, $R_7$, and $R_8$ are each independently selected from the group consisting of hydrogen; halogen; substituted or unsubstituted linear or branched alkyl having 1 to 20 carbon atoms; substituted or unsubstituted linear or branched alkenyl having 2 to 20 carbon atoms; substituted or unsubstituted linear or branched alkynyl having 2 to 20 carbon atoms; substituted or unsubstituted cycloalkyl having 3 to 12 carbon atoms; substituted or unsubstituted aryl having 6 to 40 carbon atoms; substituted or unsubstituted alkoxy having 1 to 20 carbon atoms; and substituted or unsubstituted carbonyloxy having 1 to 20 carbon atoms.

7. A preparation method of a photoreactive polymer of claim 4, the preparation method comprising: performing an addition polymerization reaction of a monomer represented by the following Chemical Formula 1 in the presence of a catalyst composition containing a precatalyst including a transition metal in Group 10 and a cocatalyst to form the repeating unit of Chemical Formula 2a claimed in claim 4:

[Chemical Formula 1]

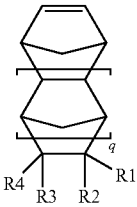

in Chemical Formula 1, q, R1, R2, R3, and R4 are as defined in Chemical Formula 2a.

8. A preparation method of a photoreactive polymer of claim 4, the preparation method comprising: performing a ring-opening polymerization reaction of a norbornenol- or norbornenalkylol-based monomer in the presence of a catalyst composition containing a precatalyst including a transition metal in Group 4, 6 or 8 and a cocatalyst to form a ring-opened polymer; and introducing a photoreactive group represented by the following Chemical Formula 1a in the ring-opened polymer to form a repeating unit represented by the following Chemical Formula 2b:

[Chemical Formula 1a]

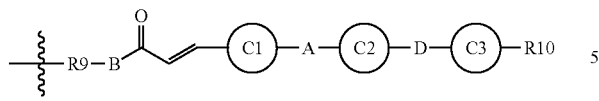

[Chemical Formula 2b]

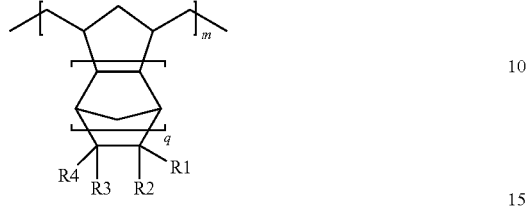

each symbol in Chemical Formula 1a is as defined in claim 1, and each symbol in Chemical formula 2b is as defined in claim 4.

9. The preparation method of a photoreactive polymer of claim 8, wherein in the performing of the ring-opening polymerization reaction, a hydrogenation reaction is performed on a double bond in a norbornene ring, such that the ring-opening and polymerization are performed.

10. An alignment layer comprising the photoreactive polymer of claim 4.

11. A liquid crystal retardation film comprising the alignment layer of claim 10 and a liquid crystal layer on the alignment layer.

12. A display device comprising the alignment layer of claim 10.

* * * * *